United States Patent
Lang et al.

(10) Patent No.: US 6,585,652 B2
(45) Date of Patent: Jul. 1, 2003

(54) MEASUREMENT OF OBJECT LAYER THICKNESS USING HANDHELD ULTRA-SONIC DEVICES AND METHODS THEREOF

(76) Inventors: Philipp Lang, 36 Fairlawn La., Lexington, MA (US) 02420; John D. Mendlein, 100 University Avenue, Toronto, Ontario (CA), M5J 1V6

( * ) Notice: Subject to any disclaimer, the term of this patent is extended or adjusted under 35 U.S.C. 154(b) by 0 days.

(21) Appl. No.: 10/207,707

(22) Filed: Jul. 29, 2002

(65) Prior Publication Data

US 2003/0078498 A1 Apr. 24, 2003

Related U.S. Application Data

(63) Continuation of application No. 09/273,586, filed on Mar. 22, 1999, now abandoned, which is a continuation of application No. PCT/US97/18993, filed on Oct. 21, 1997, which is a continuation-in-part of application No. 08/731,821, filed on Oct. 21, 1996, now Pat. No. 5,941,825.

(51) Int. Cl.[7] ................................................. A61B 8/00
(52) U.S. Cl. ...................................... 600/449; 600/447
(58) Field of Search ............................... 600/437, 442, 600/443, 449, 587, 475, 310, 473; 73/624, 626; 386/402

(56) References Cited

U.S. PATENT DOCUMENTS

| | | | | |
|---|---|---|---|---|
| 4,669,482 A | * | 6/1987 | Ophir | 600/449 |
| 5,316,003 A | * | 5/1994 | Stouffer | 600/459 |
| 5,613,493 A | * | 3/1997 | Schafer | 600/442 |
| 6,456,870 B1 | * | 9/2002 | Rennert et al. | 600/475 |

\* cited by examiner

*Primary Examiner*—Francis J. Jaworski
*Assistant Examiner*—Maulin Patel
(74) *Attorney, Agent, or Firm*—Hale and Dorr LLP

(57) ABSTRACT

The present invention provides for a method of measuring layer thickness in an object comprising 1) transmitting at least a first and a second ultra-sonic pulse from at least a first and second position, 2) measuring at least one reflective distance from the first pulse and at least one reflective distance from the second pulse, wherein the reflective distance is from the object's external surface (or probe) to a reflective interface of at least one layer, 3) selecting the reflective distance having the shortest reflective distance to indicate the distance between the external surface (or probe surface) and the reflective interface of at least one layer, wherein the selecting of the shortest reflective distance reduces ultra-sonic transmission parallax of the first and second pulses relative to a plane in the object.

34 Claims, 6 Drawing Sheets

MEASUREMENT OF OBJECT LAYER THICKNESS USING HANDHELD ULTRA-SONIC DEVICES AND METHODS THEREOF

CROSS TO RELATED APPLICATION

This application is a continuation application claiming the benefit of an earlier filing date under 35 U.S.C. Section 120 of PCT application PCT/US/97/18993 filed Oct. 21, 1997 and a continuation-in-part application claiming the benefit of an earlier filing date under 35 U.S.C. Section 120 of application Ser. No. 08/731,821 filed Oct. 21, 1996.

TECHNICAL FIELD

The invention relates to the measurement of adipose tissue using ultra-sonic methods, compositions and devices, particularly methods, compositions and devices that permit adjustment of parallax error associated with measuring layer thicknesses in a object, especially adipose tissue layers in a vertebrate.

BACKGROUND

Objects often include layers of different compositions that are difficult to measure directly and accurately. In many cases, the object's interior can not be accessed to allow for direct measurement. It may be impractical to intrude the object's interior or, if even using non-invasive techniques, it may be difficult to position the probe for accurate measurements.

For measurements of biological specimens, the thickness of underlying layers are particularly inconvenient to measure. Many such measurements are preferably taken in vivo, which makes invasive techniques impractical. If non-invasive techniques are used, they are often susceptible to operator errors and can be quite costly, as in the case of expensive medical diagnostic equipment.

In the case of body adipose tissue layers, measurements with skin calipers and water immersion tanks can be used to assess body adipose tissue. Such techniques, however, have a number of drawbacks.

Skinfold calipers use the principle that the amount of subcutaneous adipose tissue correlates to percent body adipose tissue (American College of Sports Medicine, ACSM's guidelines for exercise testing and prescription, 53–63 (1995)). With a skinfold caliper measurement, after the skin is pinched by an operator without inducing pain to the subject, the thickness of the skinfold is measured with the caliper. Caliper measurements of skinfold thickness have been used with various equations developed to predict body density and percent body adipose tissue (American College of Sports Medicine, ACSM's guidelines for exercise testing and prescription, 53–63 (1995)). Most of these equations, however, are sex-specific or only apply to certain populations. Other equations to estimate body density and percent body adipose tissue have been developed using regression models that can take into account data from larger population based studies (Jackson, A. S., Pollock, M. L., Br J Nutr, 1978: 497–504 (1978)).

Even with these improvements, however, skinfold calipers are subject to several serious sources of errors. First, skinfold caliper measurements are heavily operator dependent. The force used to pull back the skin by the operator and the location of the measurement site may vary significantly between different operators, or the same operator, resulting in poor reproducibility of measurements. Second, even though skinfold caliper measurements are based on the assumption that subcutaneous adipose tissue thickness correlates to percent body adipose tissue, skinfold calipers cannot measure the thickness of subcutaneous adipose tissue directly. Skinfold caliper measurements, instead, provide an estimate of subcutaneous adipose tissue thickness which, in turn, is then used to estimate percent body adipose tissue. Thus, two approximations are used to estimate percent body adipose tissue. Third, skinfold caliper measurements may overestimate subcutaneous adipose tissue thickness. When the skinfold is pulled back for the measurement, adipose tissue from adjacent sites can be pulled toward the measurement site causing an artificial increase in the amount of subcutaneous adipose tissue present in the selected body region. This problem is exaggerated in subjects with very elastic soft-tissue. Fourth, the inaccuracies associated with skinfold caliper measurements have lead to the use of equations requiring measurements of 3 body sites, 4 body sites, and even 7 body sites (American College of Sports Medicine, ACSM's guidelines for exercise testing and prescription, 53–63 (1995)). However, even with these adjustments the inherent inaccuracies of skinfold caliper measurements, most importantly the inability to measure subcutaneous adipose tissue thickness directly, cannot be completely compensated.

Hydrostatic weighing is commonly considered the gold standard for determining body density and estimating percent body adipose tissue. Hydrostatic weighing relies on Archimedes' principle. A body submerged in water is buoyed by a counterforce equal to the weight of the water that it displaced. Bone and muscle tissue are denser than water, while adipose tissue is less dense. Therefore, a person with low percent body adipose tissue will have higher body density and weighs more in water than a person with higher percent body adipose tissue and the same air weight. Conversely, a person with higher percent body adipose tissue for the same air weight will weigh less in water.

Although hydrostatic weighing is considered the gold standard for body adipose tissue determinations, it is subject to several sources of error. First, hydrostatic weighing requires estimation of pulmonary residual volume, which may vary significantly between individuals. Although pulmonary residual volume can be measured using pulmonary function tests, this adds extra time and expense to the procedure, which could decrease patient compliance. Second, hydrostatic weighing does not account for the variability in bone density known to exist between different individuals and races (American College of Sports Medicine, ACSM's guidelines for exercise testing and prescription, 53–63 (1995)). In patients with high bone density, hydrostatic weighing will underestimate percent body adipose tissue. Conversely, in osteoporotic patients, hydrostatic weighing may seriously overestimate percent body adipose tissue. Third, hydrostatic weighing requires large and expensive displacement chambers, and complete patient immersion in water. The technical requirements and the expense of hydrostatic weighing limit its use in frequent longitudinal measurements of percent body adipose tissue that are desirable in ambulatory patients undergoing a nutritional regime or exercise induced adipose tissue reduction. Fourth, submersion of the head underwater may be difficult or anxiety provoking for some individuals.

Consequently, the present inventors have recognized the need to provide low cost and accurate ultra-sonic devices and methods for such applications, particularly hand held devices capable of being operated by untrained operators. Methods and devices are provided herein to provide for cost effective measurements and accurate of layer thickness, such as adipose tissue layer thickness.

SUMMARY

The present invention provides for the convenient and cost effective measurement of layer thickness in an object, such as adipose tissue thickness in a human, using the appropriate ultra-sonic wave production and signal processing described herein. Previously, it was not recognized that ultra-sonic measurements of layer thickness of an object were subject to inaccurate measurements due to parallax error. Nor was it previously recognized that ultra-sonic devices dedicated to measurement of layer thickness at short interrogation depths, particularly hand-held devices for self-measurement of body adipose tissue, could accurately determine layer thickness.

Non-orthogonal ultra-sonic probe alignment with respect to the plane of the interrogated object can produce an error in the measurement of layer thickness, particularly layer thickness measurements at short interrogation depths. Non-orthogonal probe alignment typically occurs when the probe transmission axis is less than 90 degrees with respect to the object plane, which has a reference angle β of 0 degrees as shown in FIG. 1. When the transmission angle is less than 90 degrees, the probe transmits and receives ultra-sonic waves over a longer than intended path that can traverse an underlying layer (or layers) of an object, which can lead to a transmission parallax error in estimating layer thickness.

The present invention provides for a method of measuring layer thickness in an object comprising: 1) transmitting at least a first and a second ultra-sonic pulse from at least a first position and a second position, 2) measuring at least one reflective distance from the first pulse and at least one reflective distance from the second pulse, wherein the reflective distance is from the object's external surface (or probe) to a reflective interface of at least one layer, 3) selecting the reflective distance having the shortest reflective distance to indicate the distance between the external surface (or probe surface) and the reflective interface of at least one layer, wherein the selecting of the shortest reflective distance reduces ultra-sonic transmission parallax of the first and second pulses relative to a plane in the object.

In another embodiment, the invention provides for a method of measuring body adipose tissue, comprising 1) transmitting at least a first and a second ultra-sonic pulse from at least a first and second position, 2) measuring at least one reflective distance from the first pulse and at least one reflective distance from the second pulse, wherein the reflective distance is from the skin to 1) an adipose tissue/muscle or 2) an adipose tissue/fascia interface, and 3) selecting the reflective distance having the shortest distance to calculate the distance between the inner or outer border of subcutaneous adipose tissue, wherein the selecting of the reflective distance helps correct for an ultra-sonic transmission parallax of the first and second pulses relative to a plane in the subcutaneous adipose tissue.

The invention can include three different methods (with the corresponding devices) for varying the transmission angle: 1) mechanically changing position of the transducer(s), 2) providing multiple transducers with predetermined positions that correspond to predetermined transmission angles and 3) steering ultra-sonic beams from multiple ultra-sonic sources (typically arrays) with predetermined firing sequences.

In one embodiment, the invention provides for a compact, cordless hand held device comprising a first ultra-sonic source with a first detector that receives an alpha ultra-sonic signal and the second ultra-sonic source with a second detector that receives a beta ultra-sonic signal. The first and second ultra-sonic detectors may be configured to detect the alpha or the beta ultra-sonic signals either individually or collectively. The first ultra-sonic source provides for a pulse with a first transmission angle and the second ultra-sonic source provides for a pulse with a second transmission angle, wherein the second transmission angle improves the measurement of a shortest reflective distance compared to the measurement of a shortest reflective distance in the absence of the second transmission angle. Alternatively, the first and second ultra-sonic sources are at least one linear array of ultra-sonic crystals that can be sequentially timed to improve measurement of the shortest reflective distance compared to the measurement of the shortest reflective in the absence of the sequential timing. Preferably, the ultra-sonic system is contained within a autonomous, hand-held housing that does not require an external connection to another device. Such devices are particularly useful for self-examination by individuals.

The ultra-sonic system may optionally comprise a computational unit that corrects for nonorthogonal probe alignment, wherein the computational unit permits computational determination of a shortest reflective distance. Typically, the computational unit will be a chip programmed to calculate reflective distance and the shortest reflective distance. For example, the computational unit can be programmed to calculate the shortest reflective distance in a human based on reflective distances from the 1) a skin/adipose tissue interface and 2) an adipose tissue/muscle or adipose tissue/fascia interface.

DEFINITIONS

Figure 1:
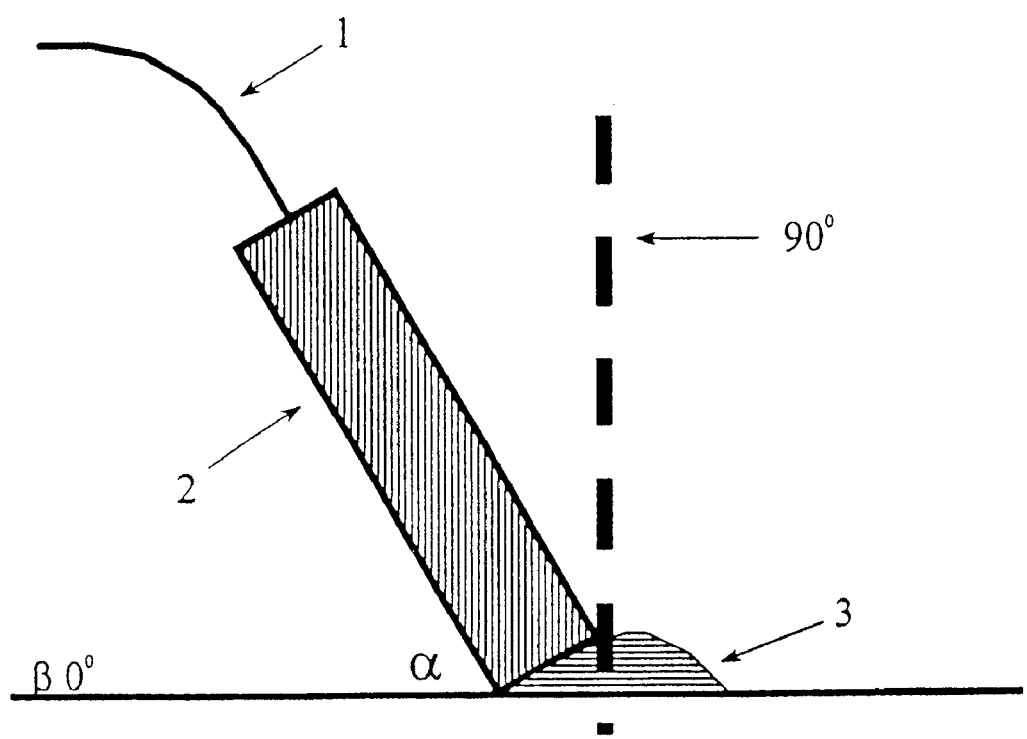
FIG. 1 shows an object plane relative to an ultra-sonic probe 2 with an acoustic coupling gel 3 between the probe 2 and the object plane and having a connection 1 to signal processing unit (not shown). The reference angle of the object's plane is 0 degrees (β). A 90 degree transmission angle is shown by the imaginary line perpendicular to the object plane.

Ultra-sonic source refers to any structure capable of generating an ultra-sonic wave or pulse, currently known or developed in the future. Crystals containing dipoles are typically used to generate an ultra-sonic wave above 20 khz. Crystals, such as piezoelectric crystals, that vibrate in response to an electric current applied to the crystal can be used as an ultra-sonic source. As referred to herein, an ultra-sonic source usually has a particular transmission angle associated with it. Consequently, a single ultra-sonic generator, as defined herein, can be used at different transmission angles to form more than one ultra-sonic pulse at different transmission angles. An ultra-sonic generator can include single or multiple ultra-sonic sources that can be arranged at different angles to produce ultra-sonic beams (or pulses) with variable transmission angles. In some ultra-sonic generators, multiple ultrasonic sources may be arranged in a linear fashion. This arrangement of ultra-sonic sources is also referred to as a linear array. With linear arrays, ultra-sonic sources are typically fired sequentially, although simultaneous firing of groups of adjacent ultra-sonic sources or other firing patterns of individual or groups of ultra-sonic sources with various time delays can be achieved as described herein or developed in the art. The time delay between individual or group firings can be used to vary the depth of the beam in an object.

Transmission angle refers to the angle of an ultra-sonic beam that intersects the object or tissue plane. The transmission angle is normally measured with respect to the object or tissue plane. The object or tissue plane has a reference angle of zero degrees.

For example, as the transmission angle increases toward 90 degrees relative to the tissue plane, the ultra-sonic beam approaches an orthogonal position relative to the tissue plane. Preferably, ultra-sonic measurements of the adipose tissue/muscle tissue interface are performed when the ultra-sonic beam is orthogonal to the plane of the tissue. Operator error, however, often leads to a parallax between the object or tissue plane and the probe. Tissue/probe parallax most often occurs when an operator fails to place the outer probe surface parallel to the tissue plane. Thus, the operator inadvertently creates a transmission angle less than ninety degrees with respect to the tissue plane, i.e. not orthogonal to the tissue plane, that skews the ultra-sonic beam and the return signal. The resultant skewing creates a parallax when using an ultra-sonic beam to measure tissue thickness, such as subcutaneous adipose tissue thickness or any other thickness measurement of a layer in an object.

Non-orthogonal ultra-sonic beam transmission creates an apparent displacement of the ultra-sonic beam compared to an ultra-sonic beam transmitted at 90 degrees with respect to the tissue plane. The return signal, which is a fraction of an ultra-sonic beam that is reflected at a tissue interface, travels through the tissue along a longer distance when returning back to the ultra-sonic detector compared to a return signal that originated from a beam transmitted orthogonal to the tissue plane. To increase the accuracy of the measurement of tissue thickness, preferably the transmission angle is between 90 to 60 degrees, more preferably 90 to 80 degrees. Lower transmission angles can be used, as low as 1 degree, but are not preferred due to the large error associated with the distance measurements of the adipose tissue/muscle tissue interface.

Ultra-sonic transmission parallax refers to an error in the measurement of distances between two distinct layers in an object, such as tissue, resulting from non-orthogonal probe placement. Ideally, the probe is oriented orthogonal to the object or tissue to be measured. In this fashion, the distance between two tissue layers measured on the ultra-sonic device will more accurately reflect the true anatomic distance. However, if the probe is applied to the skin at an angle smaller or greater than 90 degrees artifactual elongation of all measured distances will result. The difference between the distance measured with ultra-sonic interrogation and the true anatomic distance at the point where the probe is placed will increase the more the probe-to-skin angle differs from 90 degrees.

Generally, tissue thickness, especially subcutaneous adipose tissue thickness, can be measured using more than one ultra-sonic source (e.g. at least a first and second ultra-sonic source) to permit multiple transmission angles or one ultra-sonic source positioned at different transmission angles. The use of multiple transmission angles facilitates the determination of the shortest reflective distance. If only one transmission angle is used to calculate the shortest reflective distance, the shortest reflective distance could have a considerable ultra-sonic transmission parallax error associated with it.

For example, if an ultra-sonic probe transmits a beam at 60 degrees with respect to the tissue plane, a 30 degree parallax error will develop. If the subcutaneous adipose tissue thickness is actually 5 cm in thickness, the apparent thickness of the subcutaneous adipose tissue will be 5+x cm, where x is related to the number of degrees of parallax, as described in Equation 2. This difference in the actual and measured thickness of the subcutaneous adipose tissue thickness cannot be cured by signal averaging the return signals from multiple beams because each beam is sent an angle 30 degrees from perpendicular. Although the signal averaging might produce a more reproducible shortest reflective distance, the averaged shortest reflective distance will contain a significant error due to parallax. Consequently, a calculation of body adipose tissue using such an averaged shortest reflective distance without parallax adjustment will result in a substantial overestimation of body adipose tissue.

Plane refers to the surface of a cross-sectional area of tissue interrogated by an ultra-sonic probe. With ultra-sonic interrogation, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension reflects tissue depth from the plane, e.g. the distance from the skin surface to a reflection point in the tissue. The y-dimension (or depth of the interrogation) depends, among other things, on the type of transducer, the type of tissue, and the frequency with which the ultra-sonic beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm.

Tissue volume may contain several different layers of tissue, such as skin, subcutaneous adipose tissue, fascia, muscle, bone, internal organs and other tissues. Ideally, an ultra-sonic generator is oriented in an orthogonal fashion relative to the interrogated tissue. However, when an ultra-sonic generator is oriented to the skin in a non-orthogonal fashion, i.e. when the transmission angle is less than 90 degrees, a parallax can result that will artifactually increase the apparent thickness of the interrogated tissue layers.

Detector refers to any structure capable of measuring or detecting an ultra-sonic wave or pulse, currently known or developed in the future. Crystals containing dipoles are typically used to measure ultra-sonic waves. Crystals, such as piezoelectric crystals, shift in dipole orientation in response to an applied electric current. If the applied electric current fluctuates, the crystals vibrate to cause an ultra-sonic wave in a medium. Conversely, crystals vibrate in response to an ultra-sonic wave which mechanically deforms the crystals, which changes dipole alignment within the crystal, which, in turn, changes the charge distribution to generate an electric current across a crystal's surface. Electrodes connected to electronic circuitry sense a potential difference across the crystal in relation to the incident mechanical pressure. Usually, the crystals will be made of lead zirconate-titanate, barium lead titanate, barium lead zirconate, lead metaniobate, lithium sulfate and polyvinylidene fluoride, or a combination thereof. Crystals or combinations of crystals with dipoles that approximate the acoustic impedance of human tissue are preferred, so as to reduce the impedance mismatch at the tissue/probe interface.

Ultra-sonic signal refers to any ultra-sonic wave measured by an ultra-sonic detector after it has been reflected from the interface of an object or tissue. Ultra-sonic signals may range in frequency between 20 kHz and 20 Mhz or higher. Preferably, for adipose tissue measurements signals range from 0.25 Mhz to 5 Mhz.

Ultra-sonic pulse refers to any ultra-sonic wave transmitted by an ultra-sonic source. Typically, the pulse will have a predetermined amplitude, frequency, and wave shape. Ultra-sonic pulses may range in frequency between 20 kHz and 20 Mhz or higher. Preferably, for adipose tissue measurements pulses range from 0.25 Mhz to 5 Mhz and more preferably from 0.5 to 2.5 Mhz (and 400 kHz increments between 0.5 and 2.5 Mhz). Ultra-sonic pulses may consist of sine waves with single frequency or varying frequencies, as well as single amplitudes and varying amplitudes. In addition to sine waves, square waves or any other wave pattern may be employed. Square waves may be obtained by adding single-frequency sine waves to other sine waves. The summation of waves can then result in a square wave pattern.

Shortest reflective distance (SRD) refers to the shortest distance between the surface of an ultra-sonic transducer and a particular layer interface in a object, such as a transducer and a subjacent tissue interface that can be measured with ultra-sonic interrogation. The shortest reflective distance represents the best approximation of the distance measured by ultra-sonic interrogation of the true anatomic distance between the surface of a transducer and a subjacent tissue interface, such as the adipose tissue/muscle tissue interface. Skin thickness can also be measured or estimated and subtracted from the SRD to calculate the adipose tissue layer thickness, as described herein. The shortest reflective distance can be measured when an ultra-sonic transducer is oriented to the tissue interface in an orthogonal fashion. The reflective distance can be calculated as:

$$RD = SOS \times t/2, \qquad [\text{Eq. 1}]$$

where RD is the reflective distance, SOS is the speed of sound in a given medium and t is the time interval between transmission of the ultra-sonic wave and return of the signal to the transducer. The shortest reflective distance can be determined by selecting the appropriate RD as described herein.

The shortest reflective distance can be determined by using at least two or preferably multiple ultra-sonic pulses, where an ultra-sonic source provides a pulse at a predefined transmission angle. Transmission angles from an ultra-sonic source typically differ by at least 1 degree. Reflective distances between an ultra-sonic source and the tissue interface in question will be measured using the formulae described herein or developed in the art. The ultra-sonic source that has the transmission angle that is closest to 90 degrees will usually yield the smallest value for reflective distance. This value is least affected by parallax between the probe and the tissue interface and is referred to as shortest reflective distance.

Calculation of shortest reflective distance refers to electronic or mathematical determination of the shortest reflective distance using the methods described herein. Reflective distance will be calculated for ultra-sonic waves obtained at various transmission angles. A computational unit can then determine which wave yielded the smallest RD value in order to select the shortest reflective distance.

Computational unit refers to any current or future software, chip or other device used for calculations, such as reflective distance calculations, now developed or developed in the future. The computational unit is capable of determining the shortest reflective distance when two or more ultra-sonic sources are employed at different transmission angles. The computational unit may also be used for controlling the ultra-sonic generator or source, for defining or varying the firing rate and pulse repetition rate (as well as other parameters related to the ultra-sonic generator or source), for measuring the reflected signal, for image reconstruction in B-scan mode and for filtering and thresholding of the ultra-sonic signal. Other applications of the computational unit to the methods and devices described herein will be recognized by those skilled in the art. The computational unit may be used for any other application related to this technology that may be facilitated with use of computer software or hardware.

Chip refers to any current and future electronic hardware device within a computational unit that can be used as an aid in controlling the components of an ultra-sonic unit including: 1) timing and synchronizing trigger pulses and subsequent transmission of ultra-sonic waves, 2) measuring and analyzing incoming ultra-sonic signals, 3) determining the shortest reflective distance generated from ultra-sonic signals reflected from multiple different ultra-sonic waves emitted at different transmission angles, 4) estimating body adipose tissue using various equations, 5) measuring various anatomic landmarks, 6) comparing data to predetermined standards and data cut-offs (e.g. electronic filtering), and 7) performing multiple other simple and complex calculations.

Non-orthogonal probe alignment refers to alignment of the probe at an angle other than 90 degrees relative to the object or tissue plane to be measured, such as the probe/skin interface or the subcutaneous adipose tissue/muscle tissue interface.

Body adipose tissue refers to adipose tissue. It can refer to, depending on the context, to adipose tissue thickness, mass or volume. Body adipose tissue can refer to total body adipose tissue which is adipose tissue mass or volume relative to an individual's/patient's total body mass or volume, respectively. An estimate of body adipose tissue can be derived by measuring subcutaneous adipose tissue thickness at multiple body sites. Total body adipose tissue can be calculated using data collected as described herein. Using measurements derived from different sites such as the abdominal wall, the thigh, the calf, the upper arm, the axilla, the chest or the back or buttock, body adipose tissue can be estimated by applying certain equations. These equations yield parameters that are a reflection of total body adipose tissue.

Body mass index refers to a parameter that is derived by measuring weight (e.g. in kilograms) and by dividing it by the square of patient height (e.g. in meters).

Subcutaneous adipose tissue refers to a tissue layer composed of adipose cells located immediately beneath the skin. The thickness of the subcutaneous adipose tissue layer is usually a direct reflection of the nutritional and exercise status of a person. Obesity can result in a marked increase of the subcutaneous adipose tissue layer. Since there is a high association between obesity and cardiovascular disease, as well as diabetes, the thickness of the subcutaneous adipose tissue layer provides not only an assessment of the nutritional status but also of the patient's general health, particularly lipid metabolism and cardiovascular fitness.

Subcutaneous adipose tissue thickness refers to the distance from the proximal surface (interior surface) of the skin to the subcutaneous adipose tissue/muscle tissue interface. Using ultra-sonic interrogation, each layer or tissue interface produces a change in acoustic impedance resulting in a partial reflection of the ultra-sonic beam (i.e. the returning beam is a signal). With A-scan technology, the distance between the probe and each interface can be determined by measuring the time required for the reflected ultra-sonic waves to return from each interface to the probe. With B-scan technology, a two-dimensional image is acquired displaying each tissue interface with a different gray level. Tissue thickness can be measured on the image by measuring the distance between interfaces. Theoretically, an interface may also be detected between the surface of the ultra-sonic probe and the skin. However, in most applications a gel is applied to the skin that reduces the difference in acoustic impedance between both layers. Skin thickness itself is usually negligible in individuals with substantial adipose tissue layers (e.g. a Body Mass Index (BMI) of 25 to 40 Kg/m$^2$) since skin ranges typically between about 0.3 cm to 1.5 cm as compared to about 4 to 40 cm for subcutaneous adipose tissue thickness in such cases. For most practical purposes the skin/adipose tissue interface is usually a minor component in such individuals. In individuals with thinner adipose tissue layers, skin thickness is preferably measured or estimated from standard thicknesses and appropriately excluded from the determination of adipose tissue layer thickness, as described herein.

Tissue refers to an organized biomaterial usually composed of cells. For nutritional regime purposes, a distinction is made between adipose tissue and lean tissue. Adipose tissue is composed of adipose cells, while lean tissue includes all other tissues except for bone.

Skin/adipose tissue interface refers to the border between the proximal surface of the skin layer and the distal surface of the subcutaneous adipose tissue layer.

Adipose tissue/muscle tissue interface refers to the border between the proximal surface of the subcutaneous adipose tissue layer and the distal surface of the muscle tissue layer.

Adipose tissue/fascia interface refers to the border between the proximal surface of the subcutaneous adipose tissue layer and a potential distal surface of the fascial tissue layer.

Muscle/internal organ interface refers to the border between the proximal surface of the muscle tissue layer and the adjacent distal surface of the internal organs.

Muscle/bone interface refers to the border between the proximal surface of the muscle tissue layer and the distal surface of the subjacent layer of bone, e.g. the femur in the thigh, the tibia or fibula in the calf, the humerus in the upper arm, or the radius or ulna in the forearm.

Inner border of subcutaneous adipose tissue refers to the interface between the subcutaneous adipose tissue and the subjacent muscle, if present, or the interface between the subcutaneous adipose tissue and the subjacent fascia, if present.

Outer border of subcutaneous adipose tissue refers to the interface between the patient's skin and the subcutaneous adipose tissue.

Acoustic mirror refers to a device that can reflect an ultra-sonic wave and re-direct the ultra-sonic wave in a predetermined manner. If the original ultra-sonic waves are transmitted at an angle $\alpha$, which is measured relative to the surface of the plane of the acoustic mirror, the reflected ultra-sonic waves will be oriented at an angle $\alpha'=180°-\alpha$ relative to the plane of the acoustic mirror.

First position refers to a position of an ultra-sonic source that detects or transmits an ultra-sonic signal or pulse, respectively. When ultra-sonic waves are reflected from different tissue interfaces, reflective distances can be measured to the first position. These reflective distances, measured from the first position, include, but are not limited to, the distance between the ultra-sonic source and 1) a skin/adipose tissue, 2) an adipose tissue/muscle or 3) an adipose tissue/fascia interface.

Second position refers to a position of an ultra-sonic source that transmits or detects an ultra-sonic pulse or signal, respectively. When the ultra-sonic waves are reflected at the different tissue interfaces, reflective distances can be measured to the second position. These reflective distances, measured from the second position, include, but are not limited to, the distance between the ultra-sonic source and 1) a skin/adipose tissue, 2) an adipose tissue/muscle or 3) an adipose tissue/fascia interface. Once reflective distances have been measured for the first and the second position (and potentially, multiple additional positions) a shortest reflective distance can be determined for each interface by selecting the position that yielded the lowest value that is not usually greater than a preset level that discards aberrant low values that are unlikely to reflect the measured object or anatomy.

Mechanically connected refers to a connection between two or more mechanical components, such as an ultra-sonic source having at least two transmission positions. A mechanical connection between two transmission positions may be accomplished using a mechanical motor to rotate or move an ultra-sonic source. Optionally, the ultra-sonic source can be rotated or moved on a track.

Mechanical motor refers to any device that can move the ultra-sonic source from a first to a second position and, if desired, to additional positions. A mechanical motor may employ a spring-like mechanism to move the ultra-sonic source from said first to said second position. A mechanical motor may also employ a hydraulic, a magnetic, an electromagnetic mechanism or any other current and future mechanism that is capable of moving the ultra-sonic source from a first to a second position.

Oscillate refers to moving the ultra-sonic source repetitively from a first to a second position or other additional positions and moving it back from the second position or other additional positions. Oscillating from the first to the second position and back may be achieved using a mechanical motor.

Frame time, when used in the context of positioning an ultra-sonic source, refers to the time that is required to move the ultra-sonic source from the first to a second position (or other additional positions) and back using a mechanical motor or other current and future devices. Frame time typically ranges from 10 ms to 500 ms.

Programmed mechanical motor refers to any motor controlled by a program, such as a program in a chip or computer. Such motors include mechanical, electrical or hydraulic devices to move an ultra-sonic source from a first to a second positions, and if desired to additional positions. The program usually defines the frame rate that the mechanical motor moves the ultra-sonic source from a first to a second position and back. If more than two positions are used, the program can move the ultra-sonic source to many different positions, as desired.

First and second magnet refers to magnets that can be used to move an ultra-sonic source from a first to a second position. Magnets may be permanent or induced by applying an electric current to the appropriate electronic device. For example, an electric current can be applied to a wire arranged in a loop or coil-like configuration and the magnetic field created can be controlled by a predetermined electrical switch. The current induces a magnetic field that can be manipulated depending on the pattern of applied current or by the design of the coil or both.

Transmission frequency refers to the frequency of the ultra-sonic wave that is being transmitted from the ultra-sonic source. Transmission frequency typically ranges between 0.2 MHz and 25 MHz. Higher frequencies usually provide higher spatial resolution. Tissue penetration decreases with higher frequencies, especially in dense adipose tissue. Lower transmission frequencies are generally characterized by lower spatial resolution with improved tissue penetration. Methods and devices for optimizing and matching transmission frequencies to the measured object's acoustic properties are described herein.

A-scan refers to an ultra-sonic technique where an ultra-sonic source transmits an ultra-sonic wave into an object, such as patient's body, and the amplitude of the returning echoes (signals) are recorded as a function of time. Only structures that lie along the direction of propagation are interrogated. As echoes return from interfaces within the object or tissue, the transducer crystal produces a voltage that is proportional to the echo intensity. The sequence of signal acquisition and processing of the A-scan data in a modern ultra-sonic instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultra-sonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultra-sonic pulse has been emitted. Thus, reflective boundaries having equal abilities to reflect ultra-sonic waves will have equal ultra-sonic signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultra-sonic signals.

B-scan refers to an ultra-sonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a supero-inferior or mediolateral direction or a combination of both. The display of multiple adjacent scan lines creates a composite two-dimensional image that portrays the general contour of internal organs.

C-scan refers to an ultra-sonic technique where additional gating electronics are incorporated into a B-scan to eliminate interference from underlying or overlying structures by scanning at a constant-depth. An interface reflects part of the ultra-sonic beam energy. All interfaces along the scan line may contribute to the measurement. The gating electronics of the C-mode rejects all returning echoes except those received during a specified time interval. Thus, only scan data obtained from a specific depth range are recorded. Induced signals outside the allowed period are not amplified and, thus, are not processed and displayed. C-mode-like methods are also described herein for A-scan techniques and devices in order to reduce the probe/skin interface reflection.

Divergent angle refers to an angle between the axes of the first and second ultra-sonic generator. The angle is a divergent angle, when the axes of the ultra-sonic pulses transmitted from an ultra-sonic generator do not converge or cross each other in the object or tissue.

Convergent angle refers to an angle between the axes of the first and second ultra-sonic generator. The angle is a convergent angle, when the axes of two or more ultra-sonic pulses transmitted from an ultra-sonic generator converge and cross each other at some point in the measured object or tissue.

Linear array refers to a transducer design where the crystals are arranged in a linear fashion along one or more axes. Crystals can be fired in sequential, as well as non-sequential and simultaneous, firing patterns or a combination thereof. With sequential firing, each crystal can produce an ultra-sonic beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Phased array imaging refers to a transducer design where the entire array produces only one line of sight each time the crystals are being fired. The direction of the beam is, however, electronically steered by altering the excitation sequence of the individual crystal elements. Steering the beam throughout the entire field of view allows for data collection along different lines of sight. The advantage of phased array transducers over sequential and segmental linear arrays is their smaller size. The crystals in a phased array transducer can be arranged in a linear, rectangular, ring or any other pattern.

Trigger pulse refers to an electrical signal relayed to a crystal or an array of ultra-sonic generating materials (e.g. piezoelectric crystals) that induce the firing of the crystals. Crystals may be fired sequentially, such as from left to right or from right to left, or simultaneously, or in any other possible pattern creating sinusoidal, rectangular and any other possible current and future wave form.

Sequential firing refers to transmission of at least two separate, distinct ultra-sonic pulses, where pulse A is fired before pulse B and both pulses are separated by a time interval, where time interval $\Delta>0$.

Simultaneous firing refers to transmission of at least two separate, distinct ultra-sonic pulses from different ultra-sonic generators at the same time.

Three series of trigger pulses, depending on the context, can refer to the use of a) a first trigger pulse inducing the linear array transducer to fire from left to right, b) a second, subsequent trigger pulse inducing the linear array transducer to fire from right to left, and c) a third trigger pulse inducing all crystals to fire simultaneously, or any order of a, b, and c. Firing the linear array initially from left to right and then from right to left will result in two separate wave forms with different transmission angles. Ultra-sonic waves transmitted at various transmission angles can then be used to determine the shortest reflective distance.

Crystal refers to the material used in the ultra-sonic transducer to transmit and ultra-sonic waves and includes any current and future material used for this purpose. Crystals typically consist of lead zirconate titanate, barium lead titanate, lead metaniobate, lithium sulfate and polyvinylidene fluoride or a combination thereof. Crystal is typically a piezoelectric material, but any material that will contract and expand when an external voltage is applied can be used, if such a material can generate ultra-sonic waves described herein and known in the art. Rapid mechanical contraction and expansion of the material generates the ultra-sonic waves. Conversely, when incoming ultra-sonic waves deform the crystal, a current is induced in the material that can be measured and, ultimately, with B-scan technology be used to reconstruct an image.

Parallax adjustment refers to a correction of distance measurements for probe mis-alignment. Parallax will result when the ultra-sonic transducer is placed on the skin in a non-orthogonal orientation thereby creating a transmission angle smaller or greater than 90 degrees. As the difference between the ideal transmission angle of 90 degrees, i.e. perpendicular probe alignment, and the actual transmission angle increases, the ultra-sonic beam has to travel along an increasingly longer path through the object thereby artifactually overestimating the actual object or tissue layer thickness. A parallax adjustment, i.e. a correction of artifactually elongated distance measurements can, however, be obtained by transmitting multiple ultra-sonic waves at different transmission angles. The ultra-sonic wave that has the transmission angle that is closest to 90 degrees will yield the smallest parallax error and therefore provide the best parallax adjustment.

Spring loaded head refers to an ultra-sonic transducer head is mounted with a spring or spring-like (or similar mechanism) compensator for parallax adjustment ("parallax compensator"). Such a device may be composed of a spiral-shaped metallic or plastic spring or any other current and future material or shape, including fluids or compressible materials that will demonstrate elastic rebound after mechanical deformation and compression. Whenever the transducer is applied to the skin, the parallax compensator will be compressed. The elastic rebound of the parallax compensator ensures constant pressure between the transducer surface and the skin. The force used to compress the spring to permit transducer contact with the surface of the interrogated object should be equal to or slightly greater than the force required to achieve sufficient acoustic coupling between the transducer and the object.

When the transducer is not mounted with a spring-like compensator, the amount of pressure applied between the transducer surface and the skin is likely to vary with each measurement and, in particular, will vary significantly between different examiners resulting in decreased reproducibility of results. Additionally, excessive applied pressure will lead to compression of the subjacent subcutaneous adipose tissue by the transducer resulting in artifactual decrease in shortest reflective distance and underestimation of body adipose tissue. Using a spring-loaded head, the pressure between the transducer surface and the skin is kept constant even between different examiners. Thus, reproducibility of repeated measurements will be improved and artifactual underestimation of body adipose tissue will be reduced.

DETAILED DESCRIPTION OF THE INVENTION

Introduction

The present invention recognizes for the first time that ultra-sonic interrogation can be applied to the convenient and cost effective measurement of layer thickness in a object, such as adipose tissue thickness in a human, using the appropriate ultra-sonic wave production and signal processing, as described herein for the embodiments of the invention. Previously, it was not recognized that ultra-sonic measurements of layer thickness of an object were subject to inaccurate measurements due to parallax error, as described herein. Nor was it previously recognized that ultra-sonic devices dedicated to measurement of near field layer thickness, particularly autonomous hand-held devices for self-measurement of body adipose tissue, could accurately determine layer thickness, as described herein.

By way of introduction, and not limitation of the various embodiments of the invention, the invention includes at least six general aspects:

1) an ultra-sonic method of measuring layer thickness in an object, particularly adipose tissue layer thickness, by obtaining the shortest reflective distance from layer interfaces to correct for non-orthogonal probe alignment on the object plane,
2) an ultra-sonic method of correcting for non-orthogonal probe alignment by mechanically varying the transmission angle of a single ultra-sonic source or generator,
3) an ultra-sonic method of correcting for non-orthogonal probe alignment by varying the transmission angle of multiple ultra-sonic sources, generators or crystal arrays by steering the transmitted ultra-sonic waves with a predetermined pattern of crystal activation, such as sequential firing,
4) an ultra-sonic method of correcting for non-orthogonal probe alignment using multiple ultra-sonic sources, generators or crystal arrays, wherein each ultra-sonic source has an individual and separate transmission angle,
5) a computational unit capable of calculating the shortest reflective distance, and if desired, capable of calculating total body adipose tissue from measured adipose tissue layer thicknesses, 6) a hand-held ultra-sonic system that includes a transducer for transmitting and receiving ultra-sonic waves for adipose tissue measurement, an electronic operating unit to control and process ultra-sonic wave generation and detection, and a display to communicate adipose tissue measurements to the operator, and 7) a spring compensated probe to reduce non-orthogonal probe alignment and object compression error.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, the invention includes a self-measurement, hand-held system and includes characteristics of aspects (6), (4) and (5). Such combinations result in particularly useful and robust embodiments of the invention.

Ultra-Sonic Methods and Devices for Measuring Body Adipose Tissue

Non-orthogonal ultra-sonic probe alignment with respect to the plane of the interrogated object can produce an error in the measurement of layer thickness, particularly near field layer thickness measurements. Non-orthogonal probe alignment typically occurs when the probe transmission axis is less the 90 degrees with respect to the object plane, which has a reference angle β of 0 degrees as shown in FIG. 1. When the transmission angle is less than 90 degrees, the probe transmits and receives ultra-sonic waves over a longer than intended path that can traverse an underlying layer (or layers) of an object. The increased transmission and reception time over-estimates the actual distance intended to be interrogated by the probe. If the transmission angle is only a few degrees off from the desired 90 degree transmission angle, the non-orthogonal probe alignment error will be relatively small. However, if the interrogated depth is short, such as 20 to 40 cm or less, non-orthogonal probe alignment errors will be proportionally larger compared to non-orthogonal probe alignment when the interrogated depth is long. If the absolute non-orthogonal probe alignment error in layer thickness measurement is 1 cm at an interrogated depth of 10 cm, the error will be proportionately five times as great as compared to an interrogated depth of 50 cm. If the transmission angle deviates about 10 to 15 degrees or more from the desired 90 degree transmission angle, the non-orthogonal probe alignment error will be relatively significant, especially with short interrogation depths.

In the case of the measurement of adipose tissue in vertebrates, non-orthogonal probe alignment can introduce sizable errors in thickness measurement as described herein, such as in the Examples. Such errors can lead to an overestimate of adipose tissue thickness at the site of interrogation, adipose tissue volume of the anatomical region represented by the site of interrogation and calculated total body adipose tissue that is based on such measurements. Further, if an ultra-sonic system is designed for operation by non-medically trained individuals or for self examination, where control of probe alignment is more difficult, the non-orthogonal probe alignment error can create tremendous inaccuracies and variability in the assessment of body adipose tissue.

Accordingly, the invention provides for a method of measuring layer thickness in an object comprising 1) transmitting at least a first and a second ultra-sonic pulse from at least a first and second position, 2) measuring at least one reflective distance from the first pulse and at least one reflective distance from the second pulse, wherein the reflective distance is from the object's external surface (or probe) to a reflective interface of at least one layer, 3) selecting the reflective distance having the shortest reflective distance to indicate the distance between the external surface (or probe surface) and the reflective interface of at least one layer, wherein the selecting of the reflective reduces ultra-sonic transmission parallax of the first and second pulses relative to a plane in the object.

The interrogated object can be any object that passes ultra-sonic waves and contains a layer (or layers) with reflective interfaces that permit reflection of ultra-sonic waves. Usually, such a layer will be at least 0.5 cm in thickness and the depth of field will be less than 100 cm. Although thinner layers and longer depth of fields can be probed by adjusting the transmitted frequency to optimize the depth of field, while taking in to account the type of transmission medium and loss of signal through the medium. Optimal frequencies can be measured by transmitting an ultra-sonic wave through the object having an artificially introduced reflective interface placed at one or more predetermined distances from the surface of the object (see also the Examples). Frequencies that permit detection of the introduced reflective interface can be determined and then be used to measure normally or naturally occurring reflective interfaces in the object.

The interrogated object will often be of biological origin and contain at least 50% water by weight, however, non-biological objects, such as plastic and rubber products, and objects with less than 50% water by weight can be interrogated using the methods and devices described herein. Biological objects include vertebrates, mammals, fish, plants, trees, fruits, processed foods (such as cheese), and vegetables. The invention is particularly well suited for use with flesh containing adipose tissue layers or deposits from a variety of animals such as cattle, pigs, fowl (including chickens and turkeys), fish and sheep. In vivo applications are also contemplated, such as adipose tissue layer measurement in humans, cattle, pigs, chickens, horses and other organisms.

In another embodiment the invention provides for a method of measuring body adipose tissue, comprising 1) transmitting at least a first and a second ultra-sonic pulse from at least a first and second position, 2) measuring at least one reflective distance from the first pulse and at least one reflective distance from the second pulse, wherein the reflective distance is from the skin to 1) an adipose tissue/muscle or 2) an adipose tissue/fascia interface, and 3) selecting the reflective distance having the shortest distance to calculate the distance between the inner or outer border of subcutaneous adipose tissue, wherein the selecting of the reflective distance helps correct for an ultra-sonic transmission parallax of the first and second pulses relative to a plane in the subcutaneous adipose tissue.

It will be desirable to place to the probe in a position that is substantially orthogonal to the object plane in order to measure layer thickness accurately. In many situations, however, probe placement will be compromised due to the accessibility of the object to the operator, or in the case of self-examination, the awkward positioning of the probe due anatomical constraints imposed by self-examination. In such situations, substantial orthogonal probe alignment can be achieved by transmitting a series of pluses at different transmission angles, usually about 5 to 10 degrees apart. If the probe was placed non-orthogonal to the object plane, at least one of the multiple transmissions angles will be substantially perpendicular to the tissue plane even if the probe is not. Typically, transmission angles can differ in 1, 2, 3, 4, 5, 6, 7, 8, 9 or 10 degree increments or multiples thereof. Preferably, a series of transmission angles will be used, as measured with respect to the object plane, such as 90, 85, 80, 75, 70, 65 and 60 degrees. It will be readily apparent to those skilled in the art that transmission angles of 90, 95, 100, 105, 110, 115 and 120 degrees will effectively compensate for the same degree of probe parallax.

In various embodiment of the invention, transmission angles can converge or diverge from an ultra-sonic source or sources. Generally, there is seldom a limitation as to whether convergent or divergent transmission angles can be used in the invention. Some applications will, however, operate more effectively by selecting the appropriate angle arrangement. To retain a narrower field of interrogation, a single ultra-sonic source can be used at relatively small divergent angles, such as no more than about a 20 to 30 degree total divergence in transmission angles. For a wider field of interrogation multiple ultra-sonic sources can be used with divergent angles. If a narrow field of interrogation is desired, multiple ultra-sonic sources can be used with convergent transmission angles.

Figure 2:
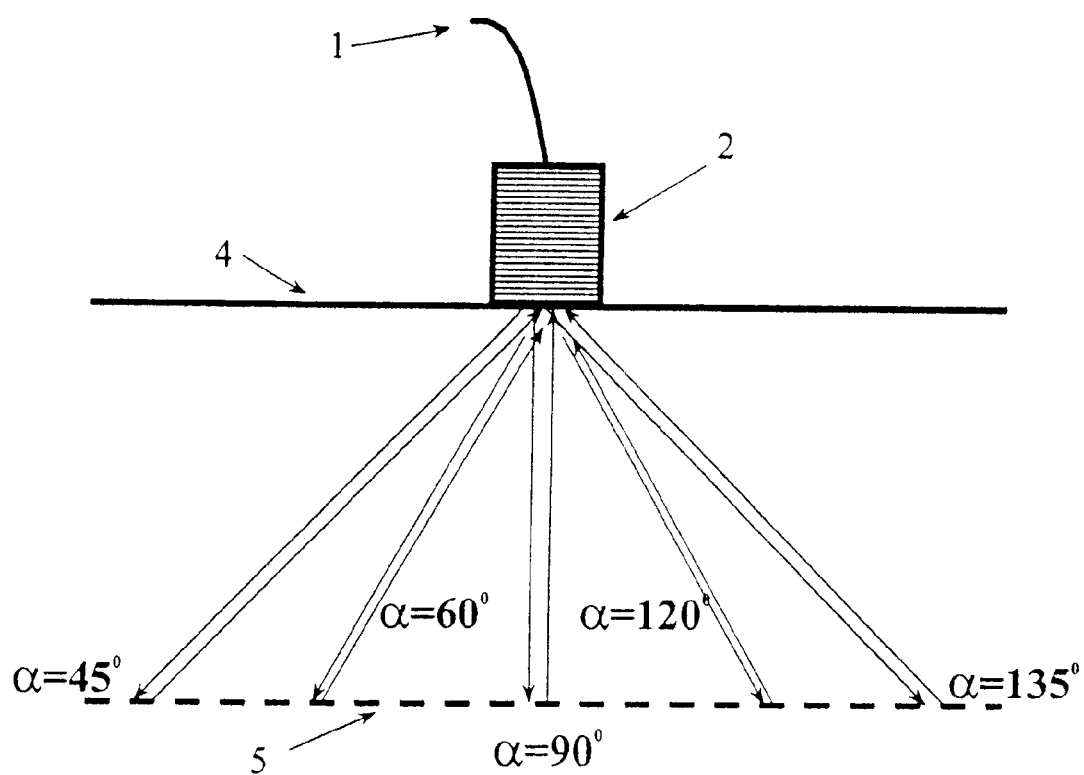
FIG. 2 shows an object plane 4 relative to a reflective interface 5 and an ultra-sonic probe 2 having a connection 1 to a signal processing unit (not shown). Five transmission angles (α) from the probe 2 are shown, 45, 60, 90, 120, and 135 degrees.

To vary transmission angles, typically a first pulse has a first transmission angle with respect to the object plane and a second pulse has a second transmission angle with respect to the object plane, wherein there is a predetermined divergent angle between the first and second pulse or a convergent angle between the first and second pulse. Reflection of the pulses from a reflective layer in the tissue is measured with an ultra-sonic detector. The predetermined divergent or convergent angles are selected to improve the measurement of a shortest reflective distance between the reflective layer and the probe compared to the measurement of a shortest reflective distance in the absence of the predetermined divergent or convergent angle. The selection of transmission angles typically takes into account the depth in the field where the target reflective layer (or layers) is likely to be located (target reflective layer depth), the likely thickness of the target reflective layer (target reflective layer thickness), object composition and distances between ultra-sonic source (if multiple source are used). Generally, the total range of transmission angles α will not be greater than 45 degrees, and preferably 30 degrees or less, as shown in FIG. 2 for example.

The divergent angle separates a first position and second position of an ultra-sonic source or sources and the first pulse has a centered first axis of transmission and the second pulse has a centered second axis of transmission, wherein the first and second axis do not converge. Usually the divergent angle between the first and second pulse is between 5 to 90 degrees, and preferably between about 5 and 20 degrees.

The convergent angle separates a first position and second position of an ultra-sonic source or sources and the first pulse has a centered first axis of transmission and the second pulse has a centered second axis of transmission, wherein the first and second axis converge. Usually the convergent angle between the first and second pulse is between 5 to 90 degrees, and preferably between about 5 and 20 degrees.

Different transmission angles can be accomplished by any method known, developed in the art or in the future or described herein. Typically, the invention includes three different methods (with the corresponding devices) for varying the transmission angle: 1) mechanically changing position of the transducer(s), 2) providing multiple transducers with predetermined positions that correspond to predetermined transmission angles and 3) steering ultra-sonic beams from multiple ultra-sonic sources (typically arrays) with predetermined firing sequences. For cost effective production of hand-held devices only one of these methods will typically be used in a device. If more sophisticated devices are desired, such methods can also be combined to gain the benefit of the different methods.

To vary transmission angles using a mechanical device, typically the first and second pulses are from a first ultra-sonic generator. The first generator has at least a first and a second position. The first and second position the are mechanically connected. The generator is guided from the first position to the second position with a mechanical connection. The first and second position (or more positions for more transmission angles) for the ultra-sonic generator can be connected using any connection that changes the transmission angle ultra-sonic generator in an accurate and controllable fashion. Typically, a sweep through all of the desired positions, either increments or continuously, should be completed within about 0.02 to 2 seconds, preferably within 200 to 500 milliseconds and more preferably within 20 to 200 milliseconds. These time values also apply to other methods of varying the transmission angle.

In one embodiment, the invention utilizes a mechanical connection comprising a mechanical motor that can oscillate a generator(s) at least once from the first to the second position (or more positions) in order to vary the transmission angle. The mechanical motor typically provides a frame time of oscillation from 10 to 2500 ms. Any mechanical motor that can produce a position change in such a time frame in response to an electrical command signal and can be adapted for use in a hand-held probe can be preferably used to vary the transmission angle of ultra-sonic generators, such as crystals or arrays of crystals.

In one design the mechanical motor has at least a first and second magnet to move the ultra-sonic generator on a track, and the generator further comprises a magnetic source or magnetically attractive material that magnetically communicates with the first or second magnet to change the transmission angle. Magnetic switching of an ultra-sonic generator position is particularly desirable because the magnet can be turned off and on relatively rapidly, and directed to change polarity relatively rapidly. Such magnetic systems can provide smooth position changes and relatively noise free performance. The track can be any mechanical device that directs the ultra-sonic generator between positions. In some instances the track will comprise a groove that engages the ultra-sonic generator and permits the ultra-sonic generator to pivot around an axis to allow for the probe to sweep across the desired transmission angles.

In another embodiment, the invention utilizes permanently fixed ultra-sonic generators with different, individual transmission angles to accomplish probe parallax reduction and the measurement of the shortest reflective distance. Typically, a first pulse is from a first ultra-sonic generator and second pulse is from a second ultra-sonic generator, wherein the first and second ultra-sonic generators are permanently fixed in a first and a second position. More than two ultra-sonic generators can be used as well but usually not more than about 10 ultra-sonic generators will be used in this embodiment, unless they are arrays of crystals.

In another embodiment, the invention utilizes predetermined patterns of ultra-sonic source activation that result in different transmission angles to accomplish probe parallax reduction and the measurement of the shortest reflective distance. For example, a predetermined pattern of ultra-sonic source activation can comprise 1) a first series of trigger pulses that sequentially fires an array of ultra-sonic crystals starting from a first end to a second end of the array and 2) a series of trigger pulses that sequentially fires the array from a second end to a first end of the array. The first series of pulses have a biased direction along a first portion of the field of the interrogated object, i.e. the beams are steered to one side of the field. This sequence of pulses can be repeated at different time frames in order to change the average transmission beam angle. Similarly, the second series of pulses have a biased direction along a second portion of the field of the interrogated object, i.e. the beams are steered to a second side of the field. This sequence of pulse can be repeated at different time frames in order to change the average beam angle. With linear arrays this method permits the use of either divergent or convergent transmission angles without mechanically moving the ultra-sonic source to change the transmission angle. Averaged beams obtained by this method with different transmission angles can then be used to calculate shortest reflective distances as described herein.

As part of the predetermined pattern of ultra-sonic source activation, simultaneous triggering pulses may also be used in conjunction with sequential firing patterns. Simultaneous firing of the ultra-sonic sources effectively provides a series of beams, which can be optionally averaged, to provide orthogonal probe position reference point. When the ultra-sonic source is orthogonal to the object plane, the transmission angle of simultaneously fired beams will be 90 ninety degrees. If the probe has a non-orthogonal position, then the transmission will be more or less than ninety degrees. By comparing the signals generated from sequentially fired pulses to simultaneously fired pulses, the deviation from an orthogonal probe position can be calculated. Comparison of the shortest reflective distance from the averaged signals of both the sequentially generated pulses and the simultaneously generated pulses will be indicative of non-orthogonal probe alignment. If so desired, this information can be transmitted back to the operator, for instance on a monitor present on the hand-held probe. Once the operator has adjusted the probe to achieve orthogonal probe alignment, additional pulses can be transmitted throughout the array and the shortest reflective distances can be measured along the array to indicate the thickness of the layer.

Figure 3:
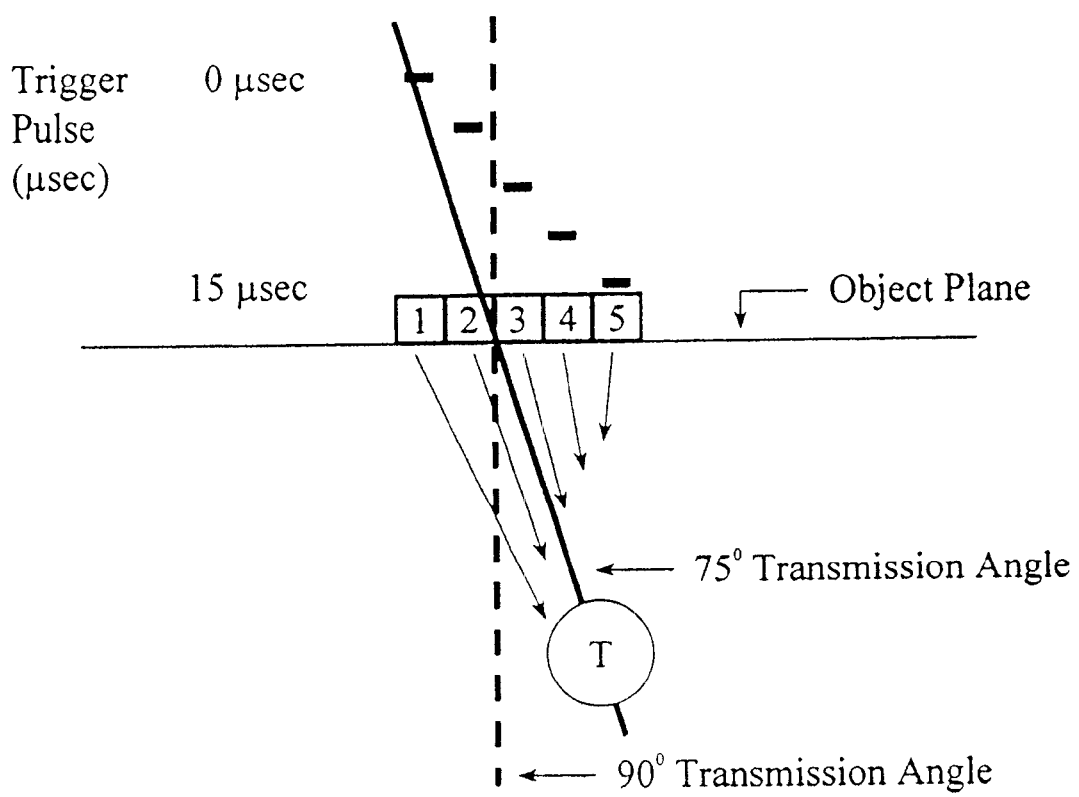
FIG. 3 shows an object plane relative to an array of ultra-sonic sources 1–5 each having a unique transmission angle, which in summation produce an average transmission angle of 75 degrees relative to tissue plane. The trigger pulse sequence is shown, which "steers" the beam to the target T.

The trigger pulses described herein can be particularly optimized to enhance measurement of shortest reflective distances in vivo, such as in humans or cattle or other objects described herein. To steer a series of beams to create an averaged beam with a specific transmission angle, each ultra-sonic crystal is triggered a 1 $\mu S$ to 500 $\mu S$ delay between the firing of each crystal. By increasing the delay between firing each crystal, the depth of interrogation and the transmission angle of the averaged beam can be increased. Ultimately, depth of interrogation will be limited by the dimensions of the transducer near field (Bushberg, J. T., Seibert, J. A., Leidholdt, E. M., Boone, J. M., The Essential Physics of Medical Imaging 1–742 (1994)). As shown in FIG. 3 the trigger pulses are timed to delay, such as an exponential delay, the firing of the crystals (crystals 1–5) over a 15 $\mu sec$ time period. The firing sequence causes a delay across the array in order to steer to the target and provide an averaged beam (of five beams in this example) with a predetermined transmission angle illustrated as 75 degrees.

The calculation of the shortest reflective distance measured at different transmission angles can be performed using a variety methodologies described herein and known in the art or developed in the future. Generally, once the signals have been received from an object, the signals are analyzed for reflective interfaces. The distances to the reflective interfaces are calculated and the shortest reflective distance is calculated from these distances. Optionally, the calculated shortest reflective distances can be further analyzed using criteria that reduces artifacts in measuring the shortest reflective distance. To calculate the reflective distance(RD) the following equation can be used: reflective distance (RD)=SOS×t/2, wherein SOS is the speed of sound, t is the total travel time of the pulse from the probe to the reflective interface and of the signal from the reflective interface back to the probe.

Typically, the shortest reflective distance can be measured as follows:

1) record signals returning from transmitted pulses reflected by reflective interfaces,
2) determine elevated signal amplitudes indicative of reflective interfaces as a function of travel time,
3) calculate reflective distances to reflective interfaces, and
4) determine the shortest reflective distance from the reflective distances.

If a returning signal contains multiple amplitudes indicating multiple reflective interfaces, the reflective distances can be calculated and the difference in distances between the interfaces can be calculated. The shortest reflective distance includes reference to the shortest distance measured between the reflective interfaces. For instance, if the signal has a first and a second reflective distance (e.g. a skin/adipose tissue interface and an adipose tissue/muscle tissue interface), the first reflective distance subtracted from the second reflective distance is the thickness of the layer between the two interfaces. The layer thickness can be compared to the layer thickness calculated from other signals with a first and second reflective distance. The shortest reflective distance between the set of first and second interfaces will be indicative of the layer thickness. This type of thickness calculation is preferably applied to situations where a set of first and second interface reflective distances is obtained at different transmission angles to more accurately correct for probe parallax.

To record signals returning from transmitted pulses reflected by reflective interfaces, any ultra-sonic device can be used that can measure reflective interfaces. In A-Scan mode the reflective interfaces will appear as a peak in amplitude appearing at a particular time point. In B-Scan mode the reflective interfaces will appear as a peak in amplitude associated with a particular two dimensional region. The increase in amplitude can be measured using commonly established techniques or as described herein. For instance, if the layer of interest is thought to reside 1 to 2 cm beneath the object surface, the signal can be sampled at times starting after the anticipated reception of signals for reflective interfaces at 1 to 2 cm. By selecting a signal sampling window for a time frame that corresponds to likely depth of a reflective interface, unwanted noise and signals from interfaces that are not of interest can be eliminated.

To determine elevated signal amplitudes indicative of reflective interfaces as a function of time, the signals from the object are usually analyzed to distinguish background noise from signals originating from the reflection of ultra-sonic pulses from a reflective interface. Typically, the signal can be filtered to remove unwanted noise from scattering of the ultra-sonic pulses and interfering ultra-sonic waves. It will often be desirable to set a threshold level for detecting signals indicative of reflective interfaces to remove background noise and reduce the likelihood of obtaining false reflective interfaces. Threshold levels will vary depending on the object being interrogated, the expected acoustical impedance mismatch between mediums at the reflective interface, and the background noise. Typically, threshold levels will be at least about three to four times the average background noise.

Usually, signal amplitudes will be measured by an ultra-sonic crystal that transmitted an ultra-sonic pulse. There is no requirement, however, that an ultra-sonic detector is also an ultra-sonic source. For instance, due to signal sampling complications, it may be preferable to have pairs of ultra-sonic sources and detectors. Each pair is composed of an ultra-sonic source that transmits an ultra-sonic pulse and an ultra-sonic detector disposed relative to the ultra-sonic source to allow for detection of an ultra-sonic signal originating from the ultra-sonic source. In such a pair, the ultra-sonic detector only receives signals and does not transmit signals. Alternatively, an ultra-sonic source may act as an ultra-sonic detector and receive signals generated from its own ultra-sonic pulses, ultra-sonic pulses received from other ultra-sonic sources or a combination thereof. Preferably, in systems where the transmission angles are generated using mechanical devices, the ultra-sonic source detects a signal generated from its own pulse. These embodiments of the invention do not necessarily have to be used in shortest reflective distance measurements.

To calculate reflective distances to reflective interfaces signal, the travel time to the signal amplitude is measured and the RD is calculated as described herein or known in the art or developed in the future. The reflective distances can be calculated according to the RD equation as described herein and the RD's can be averaged if so desired. If averaging of RD's is conducted, the RD's are usually averaged on a detector by detector basis for a given transmission angle or transmission angle by transmission angle basis. For example, the RD's from a first detector (or transmission angle) are all averaged and the RD's from a second detector are all averaged. The averaged RD's from the first and second detector are then compared and the shortest reflective distance selected based on the averages of the first and second detector.

In another embodiment of the invention, layer thickness of muscle can be determined. The method of measuring muscle thickness can comprise transmitting at least a first and a second ultra-sonic pulse from at least a first and a second transmission angle with respect to a plane of a body. A first reflective distance from the skin to at least a 1) an adipose tissue/muscle or 2) an adipose tissue/fascia interface from each of the at least two pulses is measured and a second reflective distance from the skin to at least 1) a muscle/bone or 2) a muscle/internal organ interface from each of the at least two pulses is measured. A first reflective distance with the shortest distance between the inner and outer border of subcutaneous adipose tissue is selected to use in a calculation of muscle thickness. A second reflective distance with the shortest distance between the outer border of subcutaneous adipose tissue and inner border of muscle tissue is selected to use in a calculation of muscle thickness. The selection of the shortest reflective distances corrects for an ultra-sonic transmission parallax of the pulses relative to the plane. Measurement of muscle thickness is an example of the measurement of multiple thicknesses in an object since the adipose tissue layer thickness is usually measured to measure muscle thickness.

In many applications of the methods described herein, the interrogated object may have a surface layer or near surface layer of a predictable thickness. A near surface layer pertains to a layer beneath the surface of the object that is no more from the surface than 10 to 25% of the total distance of the interrogated field. Usually, such layers are within the first 1 to 20 cm from the surface of the object. If the surface layer or near surface layer of an object has a predictable thickness, such layer thicknesses can be appropriately subtracted from the reflective distances to calculate the target layer thickness. If the method and device are configured to filter out or reject the reflective interfaces' of surface or near surface layers, then subtraction of the thickness of such layer from the overall target layer thickness is particularly desirable. For example, in many applications involving adipose tissue thickness measurements the skin thickness will be predictable and can be subtracted out without the necessity of measuring. This approach provides the advantage of simplifying the pulse acquisition protocol by reducing the analysis of peak amplitudes, thereby minimizing the calculation of reflective distances.

The ultra-sonic system described herein can include at least one first ultra-sonic detector that is electronically gated to reject at least one ultra-sonic echo (signal) during at least one predetermined time interval. This is one method for reducing unwanted signals from a predictable predetermined thickness layer. The predetermined time interval is selected to improve measurement of body adipose tissue at a predetermined tissue depth compared to the absence of electronically gating of at least one first ultra-sonic detector. For example, signals are excluded from acquisition during a specified time period. The predetermined time interval can be selected automatically or manually to measure body adipose tissue at a predetermined tissue depth. The predetermined time interval will usually have an upper limit between about 1 to 60 microseconds. Preferably, the predetermined time interval is 1) between 0 to 5 microseconds or 2) greater than 40 microseconds.

The ultra-sonic system can include at least one first ultra-sonic detector that can be electronically gated with an electronic filter. Preferably, an ultra-sonic detector is electronically gated with a digital filter. The gating can be accommodated by a computational unit with a digital filter.

In addition to calculation of total body adipose tissue as described herein, measurements of adipose tissue thickness are useful for diagnosing general fitness and health. In many instances, it will not be necessary to calculate total body adipose tissue in order to obtain a clinically relevant measure of health. Adipose tissue thickness alone can be a clinically relevant measure of health. Deposition of adipose tissue at the herein mentioned sites can vary between sites. Intersite variation, such as adipose tissue thickness difference between the abdomen and upper thigh, can be used to follow relocation of adipose tissue storage sites in the body. In fitness, nutritional, medication or other health or medical regimes, increases or decreases in adipose tissue storage can be locally measured and tracked using adipose tissue thicknesses as the relevant marker. For instance if an individual is particularly interested in tracking reduction of abdominal adipose tissue, accurate measurements of abdominal adipose tissue thickness are afforded unlike other techniques, such as water displacement or specific gravity measurements. In another example, the effect of adipose tissue reducing or appetite inhibiting agents, such as amphetamine derivatives, and surgical techniques, such as liposuction or bowel surgery, can be monitored at different sites of the body. Similarly, measurements of muscle thickness are useful for monitoring fitness and health in individuals and for monitoring the effect of muscle increasing or decreasing agents.

Ultra-Sonic Devices for Measuring Layer Thickness

The present invention includes ultra-sonic systems for measuring layer thickness as described herein. Typically, a compact ultra-sonic system will be used in parallax adjustment that has an ultra-sonic source configured to transmit ultra-sonic pulses at different transmission angles. The ultra-sonic system usually comprises at least a first and a second ultra-sonic source. The first ultra-sonic source provides a first pulse with a first transmission angle with respect to a plane of an object and the second ultra-sonic source provides a second pulse with a second transmission angle with respect to the plane of the object. This enables the transmission of pulses for reflective distance measurements at different transmission angles.

In one embodiment, the first ultra-sonic source has a first detector that receives an alpha ultra-sonic signal and the second ultra-sonic source has a second detector that receives a beta ultra-sonic signal. One ultra-sonic source can be used at different transmission angles to accomplish this. If such an arrangement is selected, then a single ultra-sonic source can be used as a detector to measure both the alpha and the beta pulse. The first and second ultra-sonic detectors can detect the alpha or the beta ultra-sonic signals either individually or as a pair or a combination of the two. The first transmission angle and the second transmission angle improve the measurement of a shortest reflective distance compared to the measurement of a shortest reflective distance in the absence of the second transmission angle. Alternatively, the first and second ultra-sonic sources are at least one linear array of ultra-sonic crystals that can be sequentially timed to improve measurement of the shortest reflective distance compared to the measurement of the shortest reflective in the absence of the sequential timing. Preferably, the ultra-sonic system is contained within an autonomous, hand-held housing that does not require an external connection to another device (such as a cord free probe). Such devices are particularly useful for self-examination by individuals.

The ultra-sonic system may optionally comprise a computational unit that corrects for non-orthogonal probe alignment, wherein the computational unit permits computational determination of a shortest reflective distance. Typically, the computational unit will be a chip programmed to calculate reflective distance and the shortest reflective distance. For example, the computational unit can be programmed to calculate the shortest reflective distance in a human based on reflective distances from the 1) a skin/adipose tissue interface and 2) an adipose tissue/muscle or adipose tissue/fascia interface.

In one embodiment, the ultra-sonic system comprises a first and second source that are generated from a first ultra-sonic generator and the generator has at least a first and a second position. The first and second position are mechanically connected and the generator is guided from the first position to the second position with a mechanical connection, such as a mechanically engaged members, magnetic connections or hydraulic connections. Typically, the mechanical connection uses a mechanical motor to oscillate the generator at least once from the first to the second position. The mechanical motor can provide a frame time from 10 to 500 ms for moving the generator between positions, which can total more than two. The mechanical connection can use a programmed mechanical motor to move the generator. The motor can contain a program chip or the motor can be driven by the computational unit. Mechanical systems as known in the art and developed in the future can be used to position the generator.

Figure 4A:
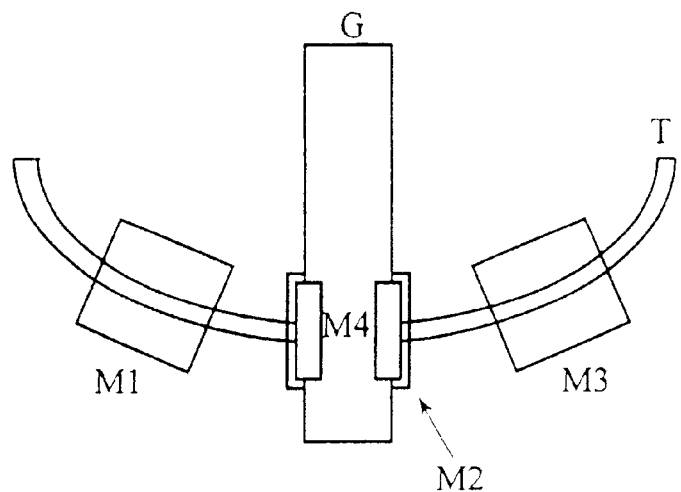
FIGS. 4A and 4B show the one embodiment to change the transmission angle of an ultra-sonic generator G using magnets M1–M3 disposed at predetermined positions on a track T and in magnetic communication with a magnet M4 disposed on the ultra-sonic generator G.
Figure 4B:
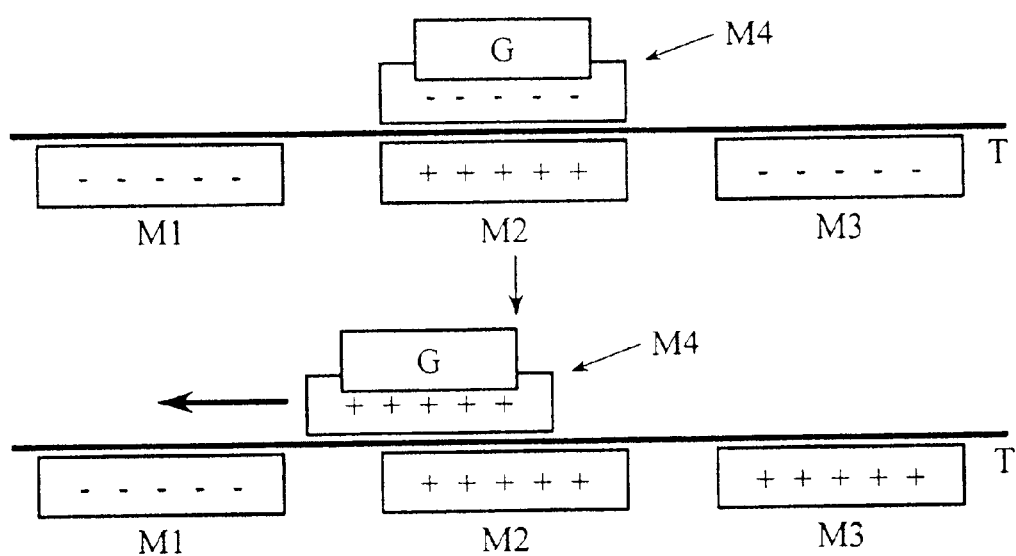

Alternatively, the mechanical motor can be at least a first and second magnet to move the generator on a track. The generator can further comprise a magnetic source or material disposed on the exterior of the generator that magnetically communicates with the first or second magnet to change the transmission angle. For example, as shown in FIG. 4 magnets M1, M2, and M3 are disposed on a track T that engages the ultra-sonic generator G. Each magnet is located in a predetermined position to enable a predetermined transmission angle for each pulse transmitted from generator G. Generator G has a magnet M4 located on it and in controllable magnetic communication with the magnets located on the track. The position of generator G can be changed by appropriately changing the polarity of the magnets on the track and the generator. By generating the appropriate magnetic field between the magnet M4 and the track magnets M1–M3, the generator can be repositioned. Other magnetic systems as known in the art and developed in the future that can be adapted to hand held, compact probes can also be preferably used.

Such magnetic positioning systems can be applied to other types of diagnostic and therapeutic probes (including x-ray probes), and X, Y (or Z) positioning systems for equipment and optical instrumentation (including lasers, other light sources, fluorescent detectors, and spectrophotometrical equipment). Magnet positioning can provide the advantage of accurate positioning (e.g. at the 10–100 micron level) by providing electrical circuits in the positioning magnets that correspond to the changes in positioning desired (e.g. 10–100 microns).

In another embodiment, the ultra-sonic system comprises at least a first and second ultra-sonic source that are permanently fixed in at least a first and a second position. In such embodiments the ultra-sonic source can also be an array fixed at different transmission angles or multiple, single ultra-sonic sources. If a particularly small transducer is desired, the ultra-sonic sources can be fixed at different planes, as well, with the transducer. Such embodiments are convenient to manufacture as they do not require movable mechanical couplings.

The ultra-sonic sources described herein can be operated using different frequencies to achieve maximal penetration and accuracy of interface reflection within the interrogated object. Typically, the ultra-sonic sources will have the same transmission frequencies. In some embodiments, however, different transmission frequencies will be desirable. For instance, different transmission frequencies are desirable when 1) the object presents multiple layers of differing densities and impedance, 2) varying sizes of microstructures cause scatter at layer interfaces and 3) sampling or filtering based on the frequency of the ultra-sonic pulses or signals is desired. Transmission frequencies can be adapted to maximize the detection of impedance mismatches between layers having different sound transmission and propagation speeds. Different transmission frequencies can also be used to influence scatter from microstructures at layer interfaces in order to improve ultra-sonic reflection appropriately by matching transmission frequency relative to the size of the microstructures. In some instances, it will be desirable to transmit at different frequencies in order to facilitate signal processing. Signals can be filtered, coded or sampled based on frequency. This permits localization of interfaces by a specific ultra-sonic source to provide more specific depth and layer thickness measurements.

For example, the ultra-sonic system can contain three ultra-sonic sources transmitting at three different frequencies and separated by predetermined distances. Detection of returning signals can include sampling of all the returning frequencies at all detector sites, which effectively allows each ultra-sonic source to be coded and the returning signals can be identified with a particular ultra-sonic source. This permits greater refinement of reflective distances because the reflective distance from each ultra-sonic source is separately detected at each detector, which facilitates signal averaging and can optionally provide a basis of triangulation between different ultra-sonic sources and the reflective interfaces in order to verify reflective distances. This essentially permits detection from multiple reflective angles. This can be accomplished by providing pairs of ultra-sonic sources and detectors, where the detectors are located adjacent to the ultra-sonic sources and can detect multiple frequencies. For instance, in the case of three ultra-sonic sources, each ultra-sonic source is disposed with a detector or detectors to receive signals from the other two ultra-sonic sources.

In many instances the first and second sources (or more) will have different transmission frequencies. The sources can be used with A-scan or B-scan or any combination thereof. Usually the source will have a set frequency of about 0.2 and 25 Mhz. In other embodiments, the sources can have variable frequencies. For example, the first source can generate at least two frequencies between 1 and 2.5 Mhz and second source can generate at least two frequencies between 0.5 and 5 Mhz. Transmission angles can be used as discussed herein.

The ultra-sonic sources can be arranged in any manner as described herein, known in the art or developed in the future. The ultra-sonic source may be an array, such as a linear or a circular array, or a linear or circular matrix. For example, the ultra-sonic system can contain matrix of ultra-sonic crystals, such as a rectangular matrix of the following formula:

A Bn C

A1 B1 C1

A2 B2n C2 wherein A, A1, A2, B, B1, B2, C, C1, and C2 are individual ultra-sonic crystals capable of transmitting an ultra-sonic pulse, and n can be equal 0 or any number between 1 and 10, preferably between 1 and 20. Trigger pulse patterns can be used to fire the matrix so as to maximize the accuracy of reflective distances. For instance, a first trigger pulse sequentially fires crystals in the array in the following order A Bn C; then A1B1n C1; then A2 B2n C2; then A A1 A2; then B B1 B2, and then C C1 and C2. The trigger pulse is timed to allow crystals in the matrix to receive ultra-sonic signals reflected from the object.

In another embodiment of the invention, the compact ultra-sonic system comprises at least a first ultra-sonic source to transmit an ultra-sonic pulse to a plane of an object, at least a first ultra-sonic detector, and means for calculating or generating the shortest reflective distance; wherein the ultra-sonic system optionally measures body adipose tissue. Optionally, the system can include an electronic computational unit that permits parallax adjustment by determining a shortest reflective distance in the object. For example the electronic computional unit can comprise a chip that permits calculation of the shortest reflective distance. Preferably, the system is hand-held, autonomous and optionally comprises an electronic operating unit to control and process ultra-sonic wave generation and detection, and a display to communicate adipose tissue measurements to the operator.

In this and other embodiments mentioned herein, an acoustic mirror can be used to produce different transmission angles. For example, the ultra-sonic system can include a first ultra-sonic source that transmits an ultra-sonic pulse with an acoustic mirror to generate at least one additional axis of transmission. Multiple transmission angles can be generated using an acoustic mirror as an inexpensive way of directing the ultra-sonic pulses.

In another embodiment of the invention, probe parallax can be reduced by mechanically orienting the probe on the surface of the interrogated object in an orthogonal fashion. Orthogonal probe placement can be accomplished with a non-orthogonal adjustment unit that reduces parallax by placing an ultra-sonic probe flush with the plane of the object. For example, the non-orthogonal adjustment unit can comprise a spring-loaded head means around the perimeter of the ultra-sonic probe. The spring-loaded head means compresses when the probe is placed flush to the surface of the object. The spring or compression device can be located in the housing of the probe to either outwardly poise the probe from the surface of the housing or to outwardly poise the housing from the surface of the probe. Ideally, the probe is allowed to "float" in the housing. The housing permits orthogonal probe placement because it would be difficult for the operator to make an acoustical connection between the probe and the object without placing the housing on the surface of the object.

Figure 5A:
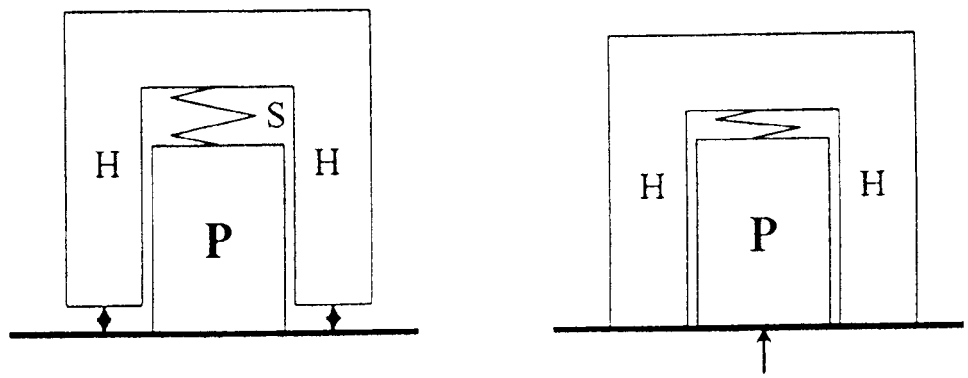
FIGS. 5A, 5B and 5C show three different embodiments of a parallax compensator that uses compressionable devices S disposed on or within a housing H and optionally disposed on the interior portion of the probe P.

For example, the compression device can be disposed on the interior surface of the probe with a support member and the probe is slideably engaged with the probe housing. The probe is slightly extended from the probe housing when the compression device is in an expanded state. When the probe contacts the surface of the object pressure is applied to the probe to make an acoustical contact with the object. As pressure is applied, the probe retracts into the housing and the compression device compresses to allow for controlled retraction. Once the probe becomes flush with the exterior surface of the probe housing, the probe is prevented from further retraction. By varying the ease of compressing the compression device, the amount of pressure applied to the interrogation site can be determined and controlled. When the probe is flush with the probe housing, the probe must be aligned orthogonal to the plan of the object, as shown in FIG. 5A.

Figure 5B:
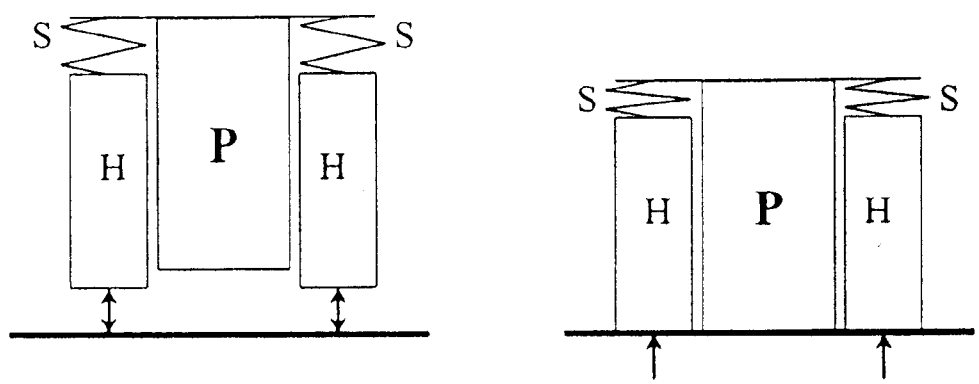
Figure 5C:
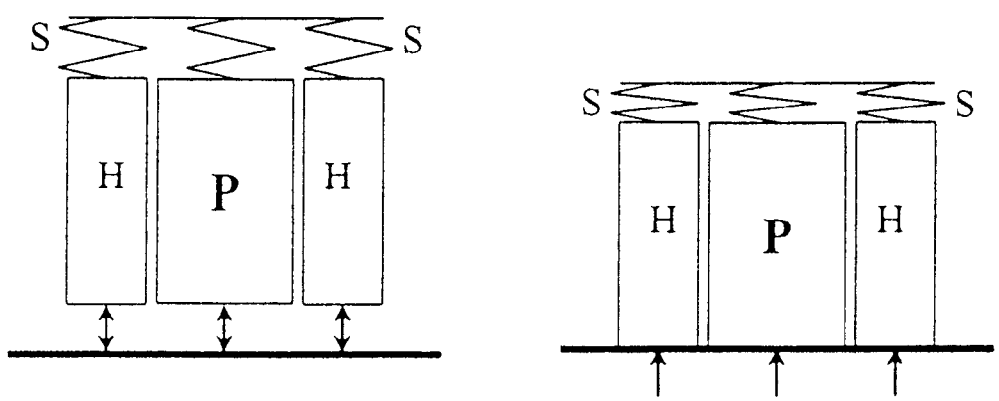

Alternatively, the compression device can be disposed on the interior surface of the probe housing with a support member that engages the posterior end of the compression device to allow the housing to extend past the probe when the compression device is in an expanded state. The probe is slideably engaged with the probe housing to allow the housing to retract when the probe is applied to the object's surface. As pressure is applied, the housing retracts until the probe makes an acoustical contact with the surface of the object. At this point the probe is flush with the exterior surface of the housing and orthogonal to the plane of the surface of the object. The compression device compresses to allow for controlled retraction as shown in FIG. 5B. If further compression of the tissue around the probe is of concern, the probe can be fitted with a second compression device to reduce tissue compression as shown in FIG. 5C.

Any of the compression device embodiments can include a switch to control probe transmission and detection. Any of the compression devices can be electrically coupled to a probe to trigger transmission and detection when the probe is flush with the housing and properly aligned. Alternatively, the probe could simply contain a contact point that aligns up with a contact point on the housing where the probe is flush with the housing to trigger transmission and detection.

The ultra-sonic system can include a pulse acquisition system comprising at least one first ultra-sonic detector that is electronically gated to reject at least one ultra-sonic echo during at least one predetermined time interval. Such a system can be used as described herein to reject or eliminate signals from known or predictable reflective interfaces. Typically, the time interval is selected to improve measurement of body adipose tissue at a predetermined tissue depth compared to the absence of electronically gating at least one first ultra-sonic detector. In the case of adipose tissue thickness measurements, at least one predetermined time interval is selected automatically or manually to measure body adipose tissue at a predetermined tissue depth. Often skin thickness will be excised form the data by electric gating. The predetermined time interval might often have an upper or lower limit between 1 to 60 microseconds. Preferably, the predetermined time interval is 1) between 0 to 5 microseconds or 2) greater than 40 microseconds. Gating can include selective data acquisition or electronic filtering of unselected data, such as an ultra-sonic detector electronically gated with an electronic filter (such as a digital filter). The pulse acquisition system can be included in the computational unit.

Kits and Computer Programs for Health Related Measurements

The present invention includes kits for monitoring reflective distances of objects especially of biological layers and tissues, such as adipose tissue, muscle, fibrotic and scar layers and tumors. For example, the kits can include an ultra-sonic system for measuring the shortest reflective distance, and at least one of the following: 1) nutritional supplements, 2) a nutrition plan, 3) a workout plan, 4) cardiovascular therapeutics, 5) weight loss agents, 6) prescription or over the counter drugs (including anti-cancer agents and hormones, e.g. steroids), 7) fitness equipment and 8) a health club membership.

The present invention includes computer programs for calculating layer thickness, shortest reflective distance and desired estimates of body composition, such as total body adipose tissue or percent body adipose tissue based on shortest reflective distance measurement of adipose tissue thickness. The computer program can be stored on any storage device such as a chip, hard drive or floppy disc. The program can be used in conjunction with a computational unit and integrated into such a unit or it can be a separate unit compatible with computers, such as personal computers. Such computer programs can optionally calculate total body adipose tissue, lean body mass (e.g. muscle mass), as well as provide a historical tracking of a user's calculated values. For example, a cancer patient may desire to track the progression or regression of a tumor layer.

EXAMPLES

General Materials and Methods

The following materials and methods are exemplary of the materials and methods that can be used to achieve the results described herein. One skilled in the art will readily recognize substitute materials and methods.

In vitro and in vivo ultra-sonic measurements were performed using an Ultramark 9 HDI ultra-sonic system (Advanced Technologies Laboratories ("ATL"), 22100 Bothell Everett Hwy, Bothell, Wash. 98041-3003). All examinations were performed using a 5 MHz linear array transducer manufactured by ATL. An acoustic coupling gel was applied to the transducer surface and the object to be examined in order to reduce the impedance mismatch between the transducer surface and the object surface, usually skin. Data were acquired in B-scan mode. Two-dimensional gray-scale images of the various tissue layers were obtained. Images were displayed on a computer monitor attached to the scanner hardware and capable of displaying the full gray scale range. Distance measurements were performed by saving a representative image displaying the various tissue layers, e.g. adipose tissue and muscle, on the display monitor. Unless otherwise indicated, a trained physician identified the various tissue interfaces visually and placed cursors manually at the skin/adipose tissue and adipose tissue/muscle or adipose tissue/fascia interface. Software provided with the ultra-sonic scanner was then used to calculate the distance between the calipers. All measurements were expressed in mm.

In both in vitro measurements in bovine and pork tissue, as well as in vivo measurements in human subjects, ultra-sonic distance measurements were performed at different transmission angles relative to the tissue surface in order to evaluate the effect of transmission angle on the accuracy of the measurement. In this fashion, measurement errors resulting from operator-induced non-orthogonal alignment of the ultra-sonic source relative to the skin or tissue surface were simulated. Transmission angles included 90 degrees, i.e. orthogonal alignment of the ultra-sonic transducer, 85, 80, 70, and 60 degrees. All transmission angles were performed relative to the skin or tissue surface. These transmission angles were achieved in a reproducible fashion by placing the ultra-sonic transducer against a specially designed biocomposite wedge with a flat undersurface which rested comfortably on the skin/tissue surface. The transducer was placed parallel and flush against the angled side of the wedge. Five wedges were used with angles of 90, 85, 80, 70, and 60 degrees, thereby defining the angle at which the ultra-sonic beam was transmitted into the tissue.

In addition to these measurements with controlled transmission angles using the biocomposite wedges, free hand measurements without transmission angle guidance were performed in in vitro experiments in bovine and pork tissue and in in vivo measurements in human subjects. In free hand measurements, the transducer was held by the person operating the ultra-sonic machine and the position and angulation of the transducer was only controlled by the operator's eye. No hardware or other devices were used in order to achieve perpendicular alignment of the transducer relative to the skin or tissue surface.

Skinfold caliper measurements were performed using a commercially available skinfold caliper (Novel Products, P.O. Box 408, Rockton, Ill. 61072). For the skinfold measurements, the skin and attached adipose tissue were pulled away from the underlying muscle by a physician person or a person trained by a physician. In all in vitro experiments, skinfold measurements were performed at the same site at which the ultra-sonic measurement was performed. In human subjects, skinfold measurements, as well as ultra-sonic measurements, were performed at the following sites: chest, abdomen, axilla, subscapular region, suprailiac region, triceps region, biceps region, anterior and posterior thigh region, and regions of the medial and lateral calf. The skinfold and ultra-sonic measurement sites were identified in the human subjects as follows:

Chest: Halfway between the right nipple and the right axilla located over the pectoralis major muscle.
Abdomen: One inch to the right of the umbilicus.
Axilla: On the right midaxillary line at the level of the xiphoid process of the sternum.
Subscapular region: One inch below the angle of the right scapula.

Suprailiac region: One inch above the right iliac crest at the level of the anterior superior iliac spine.

Triceps region: On the back of the upper right arm, halfway between the shoulder and the elbow located over the triceps muscle.

Biceps region: On the front of the upper right arm, halfway between the shoulder and the elbow located over the biceps muscle.

Anterior thigh: At the anterior aspect of the right thigh, halfway between the hip and the knee, located over the rectus femoris muscle.

Posterior thigh: At the posterior aspect of the right thigh, halfway between the hip and the knee.

Medial calf: On the medial side of the right calf at the largest part of the gastrocnemius muscle.

Lateral calf: On the lateral side of the right calf at the largest part of the gastrocnemius muscle.

To maintain the anatomic location of the selected sites, a dye was used to mark the sites on the skin of the human subjects and an echogenic metal needle was used to mark the sites in the tissue of in vitro samples.

Example 1

Mathematical Calculations of the Influence of Ultra-Sonic Transducer Parallax on Measurements of Reflective Distance The mathematical calculations presented herein evaluate the influence of tissue/ultra-sonic probe parallax on calculating reflective distance. One skilled in the art will readily recognize substitute calculations and equations. Tissue/probe parallax occurs when an operator fails to place the ultra-sonic transducer orthogonal to the tissue surface or skin. Thus, the operator inadvertently creates a transmission angle less than ninety degrees with respect to the tissue plane, i.e. not orthogonal to the tissue plane, that skews the ultra-sonic beam and the return signal. The resultant skewing creates a parallax when using an ultra-sonic beam to measure tissue thickness, such as subcutaneous adipose tissue thickness or any other thickness measurement of a material layer in an object. The return signal travels through the tissue along a longer distance when returning back to the ultra-sonic detector compared to a return signal that originated from a beam transmitted orthogonal to the tissue plane. The artifactual increase and also the absolute error in reflective distance resulting from tissue/ultra-sonic probe parallax is described as:

$$AE=[SRD/\cos(90°-\alpha)]-SRD \quad \text{[Eq. 2]},$$

where AE is the absolute error, SRD is the shortest reflective distance, i.e. the distance from the ultra-sonic probe to the tissue interface that would be measured with an ultra-sonic transmission angle of 90°, and $\alpha$ is the actual transmission angle.

The relative error (RE) in reflective distance is herein described as:

$$RE=(\{[SRD/\cos(90°-\alpha)]-SRD\}/SRD)\times 100 \quad \text{[Eq. 3]}$$

Theoretical calculations indicate that tissue/probe parallax can result in a significant overestimation of reflective distance of up to at least 40% relative error (transmission angle of 45 degrees and actual SRD of 5 cm.) The presence of tissue/probe parallax in measuring reflective distance of the subcutaneous adipose tissue/muscle tissue interface will lead to significant overestimation of body adipose tissue. Additionally, longitudinal measurements at different time intervals are difficult to compare since tissue/probe parallax may vary for different examinations. The error resulting from tissue/probe parallax can easily exceed any actual increase or decrease in subcutaneous adipose tissue thickness. Moreover, these theoretical calculations do not account for other potential, patient-specific error sources such as tissue inhomogeneity or irregularity of the tissue interfaces. Thus, much higher errors are likely to occur when tissue thickness is measured in human subjects in vivo.

Example 2

Accuracy of Ultra-Sonic and Skin Caliper Measurements of Subcutaneous Adipose Tissue Thickness in In Vitro Samples of Bovine Tissue and Comparison to Anatomic Dissection In order to evaluate the accuracy of ultra-sonic measurements and skin caliper measurements in estimating the thickness of subcutaneous adipose tissue and in order to evaluate the influence of the transmission angle in ultra-sonic measurements of subcutaneous adipose tissue layer thickness, experiments were performed with a sample of bovine adipose tissue and muscle tissue. The results of anatomic dissection of the different tissue planes and thickness of subcutaneous adipose tissue measured with skin calipers was correlated to ultra-sonic measurements. Skin caliper measurements and ultra-sonic measurements were performed with a large piece of bovine subcutaneous adipose tissue without skin and with adherent muscle tissue obtained from the gluteal region of a cow. The tissue was fresh and had not been previously frozen at the time of the examination. Five distinct regions of interest were arbitrarily identified to be examined by both skin caliper measurement, as well as ultra-sonic interrogation. The regions of interest were marked on the tissue surface using an echogenic metal needle. In this fashion, it was ensured that skin caliper and ultra-sonic measurements would all be performed in the same region. For skin caliper measurements, the subcutaneous adipose tissue was compressed by the operator using the thumb and index finger of the right hand and the skin caliper was applied with the left hand.

Two ultra-sonic measurements were obtained using the free hand technique described herein. This means the operator only used visual control to ensure orthogonal placement of the ultra-sonic transducer relative to the tissue plane and no other devices or aids were used in order to attempt orthogonal alignment. In these experiments, the operator was a physician trained in ultra-sonic techniques.

Following the free hand ultra-sonic examination of the tissue planes, ultra-sonic measurements were performed at defined transmission angles by using the wedges described herein. For this purpose, the undersurface of the biocomposite wedge was placed on the bovine tissue and the transducer was placed parallel and flush against the angled side of the wedge. Transmission angles used were 90, 85, 80, 70, and 60 degrees. The results of these experiments set forth in Tables 1 and 2.

Table 1 compares the thickness of subcutaneous adipose tissue measured by 1) anatomic dissection, 2) skinfold calipers, 3) free-hand ultra-sonic measurements and 4) ultra-sonic measurements using wedges with predefined transmission angles.

TABLE 1

| | | | | | Ultra-Sonic Measurements | | | | |
|---|---|---|---|---|---|---|---|---|---|
| Site # | Anatomic Dissect. | Skinfold Caliper | Free-Hand 1 | Free-Hand 2 | Transm. Angle 90 | Transm. Angle 85 | Transm. Angle 80 | Transm. Angle 70 | Transm. Angle 60 |
| 1 | 0.5 | 1.0 | 0.48 | 0.48 | 0.50 | 0.51 | 0.55 | 0.65 | 0.72 |
| 2 | 0.6 | 1.1 | 0.49 | 0.60 | 0.63 | 0.63 | 0.72 | 0.73 | 0.83 |
| 3 | 0.4 | 0.2 | 0.36 | 0.38 | 0.32 | 0.23 | 0.36 | 0.66 | 0.88 |
| 4 | 1.3 | 1.8 | 1.20 | 1.15 | 1.31 | 1.25 | 1.41 | 1.51 | 1.43 |
| 5 | 1.5 | 1.1 | 1.19 | 1.22 | 1.21 | 1.27 | 1.29 | 1.33 | 1.37 |

All measurements shown in cm.
"Free-Hand 1" represents the first ultra-sonic free-hand measurement.
"Free-Hand 2" represents the second ultra-sonic free-hand measurement.
"Transm. Angle" represents the ultra-sonic transmission angle in degrees using a wedge.

Table 2 shows the absolute and relative error of ultra-sonic measurements using 1) the free hand technique and 2) ultra-sonic measurements using wedges with predefined transmission angles for the different sites when compared to anatomic dissection. The absolute error is defined as:

$$AE = US - AD, \quad [\text{Eq. 4}],$$

where AE is the absolute error of the ultra-sonic measurement in mm, US is the ultra-sonic measurement of subcutaneous adipose tissue thickness in mm, and AD is the subcutaneous adipose tissue thickness determined by anatomic dissection in mm.

The relative error is defined as:

$$RE = \{(US - AD)/AD\} \times 100 \quad [\text{Eq. 5}]$$

Based on the results shown in Tables 1, 2, and 3, the mean relative error of the first series of free-hand ultra-sonic measurements performed by a trained physician on an isolated tissue was −10.5%. Presumably, free-hand measurements by an operator without experience or measurements of a living organism would result in even greater errors. The mean relative error of the second series of free-hand ultra-sonic measurements was −6.24%. Ultra-sonic measurements obtained at a transmission angle of 90°, i.e. orthogonal to the tissue plane, had a mean relative error of −6.7%. As the transmission angle decreased, i.e. the difference of the transmission angle from 90° increased, the mean relative

TABLE 2

| | | | Ultra-Sonic Measurements | | | | | | | | | | |
|---|---|---|---|---|---|---|---|---|---|---|---|---|---|
| | Free-Hand 1 | | Free-Hand 2 | | Transm. Angle 90 | | Transm. Angle 85 | | Transm. Angle 80 | | Transm. Angle 70 | | Transm. Angle 60 | |
| Site # | AE | RE | AE | RE | AE | RE | AE | RE | AE | RE | AE | RE | AE | RE |
| 1 | 0.02 | 4.0 | 0.02 | 4.0 | 0.00 | 0.0 | 0.01 | 2.0 | 0.05 | 10.0 | 0.15 | 30.0 | 0.22 | 37.2 |
| 2 | −0.11 | −18.3 | 0.00 | 0.0 | 0.03 | 5.0 | 0.03 | 5.0 | 0.12 | 20.0 | 0.13 | 21.7 | 0.23 | 38.3 |
| 3 | −0.04 | −10.0 | −0.02 | −5.0 | −0.08 | −20.0 | −0.17 | −42.5 | −0.04 | −10.0 | 0.26 | 65.0 | 0.48 | 120 |
| 4 | −0.10 | −7.7 | −0.15 | −11.5 | 0.01 | 0.8 | −0.05 | −3.85 | 0.11 | 8.5 | 0.21 | 16.2 | 0.13 | 10.0 |
| 5 | −0.31 | −20.7 | −0.28 | −18.7 | −0.29 | −19.3 | −0.23 | −15.3 | −0.21 | −14.0 | −0.17 | −13.1 | −0.13 | −8.7 |

"Free-Hand 1" represents the first ultra-sonic free-hand measurement.
"Free-Hand 2" represents the second ultra-sonic free-hand measurement.
"AE" represents the absolute error (in cm).
"RE" represents the relative error (in percent).
"Transm. Angle" represents the ultra-sonic transmission angle in degrees using a wedge.

Table 3 shows the mean absolute and mean relative errors of ultra-sonic measurements averaged over the 5 sites for 1) the free hand technique and 2) for ultra-sonic measurements using wedges with predefined transmission angles.

error generally increased. For example, mean relative error of subcutaneous adipose tissue thickness was 23.96% at a transmission angle of 70° and 39.36% at a transmission angle of 60°.

TABLE 3

| | | | Ultra-Sonic Measurements | | | |
|---|---|---|---|---|---|---|
| | Free-Hand 1 | Free-Hand 2 | Transm. Angle 90 | Transm. Angle 85 | Transm. Angle 80 | Transm. Angle 70 | Transm. Angle 60 |
| Mean absolute error in cm | −0.11 | −0.09 | −0.07 | −0.08 | 0.03 | 0.12 | 0.19 |
| Mean relative error | −10.50% | −6.24% | −6.70% | −10.97% | 2.90% | 23.96% | 39.36% |

Free-Hand 1" represents the first ultra-sonic free-hand measurement.
"Free-Hand 2" represents the second ultra-sonic free-hand measurement.
"Transm. Angle" represents the ultra-sonic transmission angle in degrees using a wedge.

These results confirm that the accuracy of ultra-sonic measurements of subcutaneous adipose tissue thickness is heavily dependent on the alignment of the ultra-sonic transducer relative to the tissue plane. Most accurate results are achieved when the transducer is properly aligned to the skin or tissue. Non-orthogonal probe alignment can result in overestimation of subcutaneous adipose tissue thickness by 40% or potentially higher.

The negative absolute and relative measurement errors that were commonly observed with the free hand technique (Tables 2 and 3) are likely the result of compression of the tissue by the ultra-sonic transducer as the transducer was not equipped with a compression compensator as described herein to minimize tissue compression. Compression of the tissue by the ultra-sonic transducer will artifactually decrease the thickness of the tissue. This is also likely to account for the decrease in mean relative error observed with a transmission angle of 85 degree when compared to a transmission angle of 90 degree. This observation generally emphasizes the need for a technique that minimizes tissue compression. Additionally, the amount of tissue compression should be kept constant so that sequential measurements obtained at different time intervals can be compared. These goals can be achieved using a compression compensator design described herein.

Example 3

In Vivo Measurements in Volunteer Human Subjects: Influence of Transmission Angle on Measuring Ultra-sonic Reflective Distance This example documents at least one type of influence of transmission angle on measuring reflective distance of tissue interfaces in vivo in human subjects. In vivo ultra-sonic measurements were performed in the abdominal region one inch to the right of the umbilicus in two healthy volunteers, i.e. subject 1 and subject 2. Ultra-sonic distance measurements from the skin/adipose tissue to the adipose tissue/muscle tissue interface reflecting the thickness of the subcutaneous adipose tissue layer were performed at different transmission angles relative to the skin surface in order to evaluate the effect of transmission angle on the accuracy of the measurement. In this fashion, measurement errors resulting from operator-induced non-orthogonal alignment of the ultra-sonic source relative to the skin or tissue surface were simulated. Transmission angles included 90 degrees, i.e. orthogonal alignment of the ultra-sonic transducer, 85, 80, 70, and 60 degrees. These transmission angles were achieved in a reproducible fashion by placing the ultra-sonic transducer flush against a specially designed biocomposite wedge as described above.

One skilled in the art can readily recognize that the results described herein can be applied to measuring any other body region, as well as to measuring other tissues or materials both in vivo, as well as in vitro.

Table 4 shows reflective distance from the skin/adipose tissue to the adipose tissue/muscle tissue interface in the abdominal region in two healthy volunteers for different transmission angles. All measurements are shown in cm.

TABLE 4

| | Transmission Angle 90 | Transmission Angle 85 | Transmission Angle 80 | Transmission Angle 70 | Transmission Angle 60 |
|---|---|---|---|---|---|
| Subject 1- Measurement Series 1 | 0.40 | 0.45 | 0.53 | 0.49 | * |
| Subject 1- Measurement Series 2 | 0.57 | 0.69 | 0.95 | 0.97 | * |
| Subject 2- Measurement Series 1 | 3.20 | 3.35 | 3.65 | 3.97 | 4.69 |
| Subject 2- Measurement Series 2 | 3.43 | 3.58 | 3.89 | 4.34 | 5.10 |

*: Technically not possible to measure (tissue interfaces not clearly identified any longer at this transmission angle) Transmission angles are shown in degrees.

Table 5 shows percent increase in reflective distance from the skin/adipose tissue to the adipose tissue/muscle tissue interface in the abdominal region in two healthy volunteers for different transmission angles relative to a transmission angle of 90 degrees, i.e. orthogonal probe alignment.

TABLE 5

| | Transmission Angle 85 | Transmission Angle 80 | Transmission Angle 70 | Transmission Angle 60 |
|---|---|---|---|---|
| Subject 1- Measurement Series 1 | 12.5% | 32.5% | 22.5% | * |
| Subject 1- Measurement Series 2 | 21.1% | 66.7% | 70.2% | * |
| Subject 2- Measurement Series 1 | 4.6% | 14.1% | 24.1% | 46.6% |
| Subject 2- Measurement Series 2 | 4.4% | 13.4% | 26.5% | 48.7% |

*: Technically not possible to measure (tissue interfaces not clearly identified any longer at this transmission angle)
Transmission angles are shown in degrees.

Tables 4 and 5 confirm that reflective distance from the skin/adipose tissue to the adipose tissue/muscle tissue interface increases significantly with decreasing transmission angles, i.e. increasingly non-orthogonal probe alignment. Since the reflective distance from the skin/adipose tissue to the adipose tissue/muscle tissue interface is a direct measure of subcutaneous adipose tissue thickness, it is apparent that non-orthogonal probe alignment and resultant measurement of tissue thickness at a transmission angle other than 90° will increase tissue thickness artificially by up to 40–50% and potentially more.

Furthermore, when transmission angles exceed certain limits, as seen in subject 1 in Tables 4 and 5, measurement of reflective distance may not even be possible any longer, since the tissue interface may be difficult to detect.

Example 4

In Vivo Measurements in Volunteer Human Subjects: Comparison of Subcutaneous Adipose Tissue Thickness Measured by Skinfold Calipers, by Ultra-Sonic Self Measurements, by Ultra-Sonic Free-Hand Measurements by Trained Operator, and by Ultra-Sonic Measurement with a 90° Transmission Angle by Trained Operator This example compares measurements of subcutaneous adipose tissue thickness using skinfold calipers and different ultra-sonic techniques in vivo in human subjects. In vivo ultra-sonic measurements were performed in different anatomic regions in two healthy volunteers, i.e. subject 1 and subject 2. Ultra-sonic distance measurements from the skin/adipose tissue to the adipose tissue/muscle tissue interface reflecting the thickness of the subcutaneous adipose tissue layer were performed at each site. Ultra-sonic measurements included self-examination by the volunteer/subject, free-hand examination by a trained operator, and ultra-sonic measurement with 90 degree transmission angle by a trained operator. In free-hand examination, the transducer was held by the trained person operating the ultra-sonic machine and the position and angulation of the transducer was only controlled by the operator's eye. No hardware or other devices were used in order to achieve orthogonal alignment of the transducer relative to the skin in the free hand experiments. A trained operator was either a physician experienced in the use of ultra-sonic imaging or a person trained by a physician experienced in the use of ultra-sonic imaging.

Table 6 shows skinfold caliper measurements, ultra-sonic self-measurements, ultra-sonic free-hand measurements by a trained operator, and ultra-sonic measurement with 90 degree transmission angle by a trained operator for different anatomic regions in subject 1. All values are shown in mm.

TABLE 6(Subject 1)

| | | Ultra-Sonic Measurements | | |
|---|---|---|---|---|
| Anatomic Region | Skinfold Caliper | Self-measurement* | Free-Hand Measurement by Trained Operator* | 90° Transmission Angle, Measurement by Trained Operator* |
| Chest | 8 | 2.3 | 2.7 | 3.1 |
| Abdomen | 30 | 4.0 | 5.0 | 5.3 |
| Axilla | 10 | 2.5 | 2.5 | 2.4 |
| Subscapular Region | 13 | 2.5 | 2.4 | 3.2 |
| Suprailiac Region | 16 | 3.8 | 4.4 | 5.1 |
| Triceps Region | 19 | 3.8 | 4.9 | 4.6 |
| Biceps Region | 40 | 1.5 | 1.5 | 2.0 |
| Anterior Thigh | 13 | 4.5 | 2.4 | 3.5 |
| Posterior Thigh | 15 | 2.2 | 5.2 | 4.9 |
| Medial Calf | 12 | 3.1 | 3.1 | 3.8 |
| Lateral Calf | 11 | 3.6 | 3.2 | 3.2 |

*: mean value obtained from two consecutive measurements
measurements in mm.

Table 7 shows skinfold caliper measurements, ultra-sonic self-measurements, ultra-sonic free-hand measurements by a trained operator, and ultra-sonic measurement wttn 90 degree transmission angle by a trained operator for different anatomic regions in subject 2. All values are shown in mm.

TABLE 7(Subject 2)

| | | Ultra-Sonic Measurements | | |
|---|---|---|---|---|
| Anatomic Region | Skinfold Caliper | Self-measurement* | Free-Hand Measurement by Trained Operator* | 90° Transmission Angle, Measurement by Trained Operator* |
| Chest | 19 | 8.5 | 7.6 | 8.8 |
| Abdomen | 35 | 31.3 | 33.6 | 33.1 |
| Axilla | 16 | 5.1 | 5.7 | 6.1 |
| Subscapular Region | 26 | 6.0 | 6.2 | 4.4 |
| Suprailiac Region | 24 | 10.9 | 10.5 | 9.9 |
| Triceps Region | 12 | 4.6 | 4.2 | 5.3 |
| Biceps Region | 10 | 6.2 | 5.4 | 3.5 |
| Anterior Thigh | 18 | 6.7 | 5.6 | 5.6 |
| Posterior Thigh | 6 | 6.9 | 5.7 | 8.0 |
| Medial Calf | 9 | 4.0 | 3.9 | 5.0 |
| Lateral Calf | 10 | 3.7 | 2.5 | 3.1 |

*: mean value obtained from two consecutive measurements
measurements in mm.

Table 8 shows relative errors (in %) of ultra-sonic self-measurements and ultra-sonic free-hand measurements by a trained operator as compared to ultra-sonic measurement with 90 degree transmission angle by a trained operator for different anatomic regions in subject 1.

TABLE 8(Subject 1)

| Anatomic Region | Self-measurement | Free-Hand Measurement by Trained Operator |
|---|---|---|
| Chest | −25.8% | −12.9% |
| Abdomen | −24.5% | −5.7% |
| Axilla | 4.2% | 4.2% |
| Subscapular Region | −21.9% | −25.0% |
| Suprailiac Region | −25.5% | −13.7% |
| Triceps Region | −17.4% | 6.5% |
| Biceps Region | −25.0% | −25.0% |
| Anterior Thigh | 28.6% | −31.4% |
| Posterior Thigh | −55.1% | 6.1% |
| Medial Calf | −18.4% | −18.4% |
| Lateral Calf | 12.5% | 0.0% |

Table 9 shows relative errors (in %) of ultra-sonic self-measurements and ultra-sonic free-hand measurements by a trained operator as compared to ultra-sonic measurement with 90 degree transmission angle by a trained operator for different anatomic regions in subject 2.

TABLE 9(Subject 2)

| Anatomic Region | Self-measurement | Free-Hand Measurement by Trained Operator |
|---|---|---|
| Chest | 3.4% | −13.6% |
| Abdomen | −5.4% | 1.5% |
| Axilla | −16.4% | −6.6% |
| Subscapular Region | 36.4% | 40.9% |
| Suprailiac Region | 10.1% | 6.1% |
| Triceps Region | −13.2% | −20.7% |

TABLE 9(Subject 2)-continued

| Anatomic Region | Self-measurement | Free-Hand Measurement by Trained Operator |
|---|---|---|
| Biceps Region | 77.1% | 54.3% |
| Anterior Thigh | 19.6% | 0.0% |
| Posterior Thigh | −13.7% | −28.7% |
| Medial Calf | −20.0% | −22.0% |
| Lateral Calf | 19.4% | 19.4% |

Table 10 shows mean percent errors for subjects 1 and 2 of ultra-sonic self-measurements and ultra-sonic free-hand measurements by a trained operator as compared to ultra-sonic measurement with 90 degree transmission angle by a trained operator averaged over selected anatomic regions.

TABLE 10

| Anatomic Region | Self-measurement* | Free-Hand Measurement by Trained Operator* |
|---|---|---|
| Chest | −14.6% | −13.3% |
| Abdomen | −15.0% | −2.1% |
| Posterior Thigh | −34.4% | −11.3% |

The results shown in Tables 8–10 indicate that ultra-sonic self-measurements and even ultra-sonic free-hand measurements by a trained operator differ markedly from those obtained with a 90 degree transmission angle by a trained operator. The two factors that are likely to account for these differences are 1) ultra-sonic beam angulation, i.e. use of transmission angles smaller than 90 degree with resultant ultra-sonic beam parallax, and 2) tissue compression by the ultra-sonic probe with resultant artifactual decrease in subcutaneous adipose tissue thickness.

As seen in Tables 8–10, negative values of percent errors were frequently encountered with both ultra-sonic self-measurements, as well as ultra-sonic free-hand measurements by a trained operator. These negative values are most likely the result of tissue compression, which is more likely to occur in a less controlled situation where either the subject performs a self-measurement or a trained operator uses no additional devices that ensure probe positioning with a 90° transmission angle and, in addition, ensuring uniform probe—skin/tissue contact without extraneous tissue compression. Tissue compression by the ultra-sonic transducer will artificially decrease the thickness of the subcutaneous adipose tissue or other tissue layers to be measured. A compression compensator as described herein can be used to 1) ensure uniform probe—skin/tissue contact, 2) to reduce tissue compression by the ultra-sonic probe with resultant artifactual decrease in subcutaneous adipose tissue thickness, and 3) by a alleviating these problems improve the comparability of measurements obtained at different time intervals.

Table 10 shows that the absolute values of the mean percent errors of ultra-sonic self-measurements are significantly greater than those of free-hand measurements by a trained operator. This indicates that both ultra-sonic beam parallax, as well as tissue compression represent a greater problem when self-measurements are performed as compared to free-hand measurements by a trained operator emphasizing the need for techniques and devices that compensate for both 1) ultra-sonic beam parallax and 2) tissue compression.

Skinfold caliper measurements grossly overestimated the amount of subcutaneous adipose tissue. In one subject, skinfold measurements obtained in the different anatomic regions were in most instances four to five times larger (or even more, e.g. biceps region in subject one was 20 times larger) than those obtained with the different ultra-sonic techniques. In subject 2, skinfold measurements, exceeded those obtained with the different ultra-sonic techniques in most instances 2–3 times. The extreme overestimation of subcutaneous adipose tissue thickness in subject 1 may be the result of higher soft-tissue elasticity when compared to subject 2. The results obtained in both subjects indicate that skinfold caliper measurements of subcutaneous adipose tissue thickness are not very accurate in determining adipose tissue thickness in vivo.

Example 5

In Vivo Measurements in Volunteer Human Subjects: Estimating Percent Body Adipose Tissue Using Ultra-Sonic Measurements as compared to Hydrostatic Weighing Method This example compares measurements of subcutaneous adipose tissue using ultra-sonic with a 90 degree transmission angle with data obtained using hydrostatic weighing. In vivo ultra-sonic measurements were performed in different anatomic regions in two healthy volunteers, i.e. subject 1 and subject 2. A technique is presented to estimate percent body adipose tissue from ultra-sonic measurements of subcutaneous adipose tissue thickness. One skilled in the art can readily recognized that the results and methods described herein can be modified with regard to the measured regions and the equations used to calculate percent body adipose tissue based on ultra-sonic measurements. The techniques and methods described in this example can be applied to estimating volume and weight of other tissues and materials in vivo and in vitro.

Hydrostatic weighing was performed using a water tank large enough to accommodate a human body and to submerge it completely under water. A scale was installed at the bottom of the tank with a surface large enough for a human subject to sit on and to rest both legs and arms comfortably on the scale. The scale was calibrated to zero when the tank was filled with water and no objects other than the water were present in the tank.

Prior to hydrostatic weighing, the volunteer's height and air body weight were determined. The volunteer was asked to climb into the water tank. The volunteer sat down on the scale, took several deep breaths, exhaled using forced expiration, and submerged the head and all other body parts under water. The volunteers body weight during underwater submersion was measured with the scale.

With hydrostatic weighing the person's bone and muscle tissue is more dense than water, while adipose tissue has a lower density than water. The density of water is 1.0 g/cm$^3$ at a temperature of 4° C., whereas adipose tissue has an average density of 0.93 g/cm$^3$. Thus, a person with higher percent body adipose tissue for the same total air body weight has a lower body density and weighs less under water, while a person with less percent body adipose tissue for the same total body weight weighs more under water.

Body density (BD) was calculated using the following formula (American College of Sports Medicine, ACSM's guidelines for exercise testing and prescription, 53–63 (1995)):

$$BD = \text{Weight in air}/[\{(\text{Weight in Air}-\text{Weight in water})/\text{Density of water}\}-\text{Residual pulmonary volume}] \quad [\text{Eq. 6}],$$

where residual pulmonary volume was estimated using standard techniques. Estimated residual pulmonary volume of subject one was 1.71; estimated residual pulmonary volume of subject 2 was 1.51. Water density was corrected for temperature. Hydrostatic weighing measurements in subject 1 were performed at a water temperature of 86° F. corresponding to a water density of 0.9957 g/cm³. Hydrostatic weighing measurements in subject 2 were performed at a water temperature of 93° F. corresponding to a water density of 0.9944 g/cm³.

The following formula was used to calculate percent body adipose tissue (%BAT) based on measured body density (American College of Sports Medicine, ACSM's guidelines for exercise testing and prescription, 53–63 (1995, Brozek, J., Grande, F., Anderson, J., Keys, A., Ann NY Acad Sci, 110: 113–140 (1963)):

$$\%BAT = (457/\text{Body Density}) - 414.2 \quad [\text{Eq. 7}]$$

Alternatively, percent body adipose tissue can be calculated using the formula published by Siri (Siri, W. E., Univ Calif Donner Lab Med Phys Rep, March: (1956)) which was, however, not used in this example:

$$\%BAT = (495/\text{Body Density}) - 450 \quad [\text{Eq. 8}]$$

Table 11 shows body weight for hydrostatic weighing and resultant estimated percent body adipose tissue for two healthy volunteers.

TABLE 11

| Body weight (in kg) submerged under water | Subject 1 | Subject 2 |
|---|---|---|
| Measurement 1 | 3.09 | 2.16 |
| Measurement 2 | 3.12 | 2.15 |
| Measurement 3 | 3.07 | 2.20 |
| Measurement 4 | * | 2.19 |
| Mean body weight submerged in water | 3.09 | 2.18 |
| Estimated Percent Body Adipose Tissue | 14.8% | 23.4% |

*: Measurement was not obtained.

In addition to hydrostatic weighing, in vivo ultra-sonic measurements were performed in different anatomic regions in both volunteers, i.e. subject 1 and subject 2. Ultra-sonic distance measurements from the skinadipose tissue to the adipose tissue/muscle tissue interface reflecting the thickness of the subcutaneous adipose tissue layer were performed at each site. Ultra-sonic measurements were performed with a 90 degree transmission angle by a trained operator using a biocomposite wedge (see General Materials and Methods). A trained operator was either a physician experienced in the use of ultra-sonic imaging or a person trained by a physician experienced in the use of ultra-sonic imaging. Mean subcutaneous adipose tissue thickness was determined for selected regions for subject 1 and subject 2 by averaging the measurements obtained in these regions (Table 12).

Table 12 shows subcutaneous adipose tissue thickness measurements in two healthy volunteers using ultra-sonic imaging with a 90 degree transmission angle in different anatomic regions and means averaged over selected regions. All measurements are shown in mm.

TABLE 12

| Anatomic Region | Subject 1 | Subject 2 |
|---|---|---|
| Chest | 3.1 | 8.8 |
| Abdomen | 5.3 | 33.1 |
| Axilla | 2.4 | 6.1 |
| Subscapular Region | 3.2 | 4.4 |
| Suprailiac Region | 5.1 | 9.9 |
| Triceps Region | 4.6 | 5.3 |
| Biceps Region | 2.0 | 3.5 |
| Anterior Thigh | 3.5 | 5.6 |
| Posterior Thigh | 4.9 | 8.0 |
| Medial Calf | 3.8 | 5.0 |
| Lateral Calf | 3.2 | 3.1 |
| Average Chest, Abdomen, Axilla, Subscapular Region, Suprailiac Region | 3.8 | 12.5 |
| Average Biceps Region, Triceps Region | 3.3 | 4.4 |
| Average Anterior Thigh, Posterior Thigh | 4.2 | 6.8 |
| Average Medial Calf, Lateral Calf | 3.5 | 4.1 |

Estimated arm length, estimated thigh length, and estimated calf length were calculated as:
Estimated arm length = Body height × 0.43 [Eq. 9]
Estimated thigh length = Body height × 0.3 [Eq. 10]
Estimated calf length = Body height × 0.28 [Eq. 11]

Table 13 shows air weight, body height, arm length, thigh length, and calf length for subjects 1 and 2.

TABLE 13

|  | Subject 1 | Subject 2 |
|---|---|---|
| Air Weight in pounds | 169.1 | 164.8 |
| Air Weight in kg | 76.7 | 74.8 |
| Body Height in cm | 191.0 | 178 |
| Estimated arm length in cm | 82.13 | 76.54 |
| Estimated thigh length in cm | 57.30 | 53.40 |
| Estimated calf length in cm | 53.48 | 49.84 |

The ultra-sonic estimated adipose tissue volume (EATV) was calculated as:

$EATV = ([\text{US Adipose Tissue Average}_{biceps\ region,\ triceps\ region} \times \text{estimated arm length} \times 2] +$ $[\text{US Adipose Tissue Average}_{anterior\ thigh\ region,\ posterior\ thigh\ region} \times \text{estimated thigh length} \times 2] +$ $[\text{US Adipose Tissue Average}_{medial\ calf\ region,\ lateral\ calf\ region} \times \text{estimated calf length} \times 2] +$ $[\text{US Adipose Tissue Average}_{chest,\ abdomen,\ axilla,\ subscapular,\ suprailiac\ region} \times (\text{body height}-\text{thigh length}-\text{calf length})]) \times F \times A$ [Eq. 12], where F is a correction factor for body habitus and A can be included as a correction factor for age and sex. The correction factor F (measured in cm) accounts for different types of body habitus. In the example presented in Tables 14 and 15, F was equal to 70 cm and A was equal to 1. This reflects a body habitus where subcutaneous adipose tissue thickness is relatively homogeneous in different body regions. F may be adjusted in subjects with different body habitus, such as individuals with more prominent, asymmetrical abdominal subcutaneous adipose tissue or asymmetrical subcutaneous adipose tissue in the thigh region. In such cases, different F's can be applied to ultra-sonic adipose tissue thickness averages from different anatomic regions.

Additionally, age and sex differences are known to affect the density and distribution of subcutaneous adipose tissue (American College of Sports Medicine, ACSM's guidelines for exercise testing and prescription, 53–63 (1995)). For this reason, correction factor A was introduced which accounts for age and sex differences. In the example presented in Table 15, A was equal to 1. This reflects density and distribution of subcutaneous adipose tissue in male subjects between 30 and 40 years of age.

The ultra-sonic estimated adipose tissue weight (EATW) was calculated as:

$$EATW = EATV \times density_{adipose\ tissue} \qquad [\text{Eq. 13}],$$

where the estimated density of adipose tissue is 0.93 g/cm$^3$.

The ultra-sonic estimated percent body adipose tissue (%BAT) was calculated as:

$$\%BAT = EATW/\text{Body Weight} \times 100 \qquad [\text{Eq. 14}]$$

Table 14 shows estimated adipose tissue volume, estimated adipose tissue weight, ultra-sonic percent body adipose tissue, and hydrostatic weighing percent body adipose tissue.

TABLE 14

|  | Subject 1 | Subject 2 |
|---|---|---|
| EATV in cm$^3$ | 11918.2 | 19200.3 |
| EATW in g | 11083.8 | 17856.3 |
| Ultra-Sonic % Body Adipose Tissue | 14.5% | 23.9% |

The percent difference between ultra-sonic percent body adipose tissue (US %BAT) and hydrostatic weighing percent body adipose tissue (HW %BAT) can be calculated as:

$$\text{Percent difference} = [(US\ \%BAT - HW\ \%BAT)/HW\ \%BAT] \times 100 \qquad [\text{Eq. 15}]$$

Table 15 shows percent body adipose tissue measured with ultra-sonic interrogation, percent body adipose tissue measured with hydrostatic weighing, and the percent difference between both techniques for subjects 1 and 2.

TABLE 15

|  | Subject 1 | Subject 2 |
|---|---|---|
| Ultra-Sonic % Body Adipose Tissue | 14.5 | 23.9 |
| Hydrostatic weighing % Body Adipose Tissue | 14.8 | 23.4 |
| Percent difference | −2.0% | 2.1% |

One skilled in the art can readily recognize that different calculations and formulas using measurements from different anatomic regions can be used to derive the ultra-sonic estimate of percent body adipose tissue similar to the formulas that have been developed by Brozek et al. (Brozek, J., Grande, F., Anderson, J., Keys, A., Ann NY Acad Sci, 110: 113–140(1963)) and Siri (Siri, W. E., Univ Calif Donner Lab Med Phys Rep, March: (1956)) for estimating percent body adipose tissue based on body density measured with hydrostatic weighing. Derivations of the technique presented in this example using larger population based studies are likely to yield similar or even improved results.

In the current example, a volume of adipose tissue was initially calculated by measuring subcutaneous adipose tissue thickness at different sites and then multiplying it with estimated length of the measured region and a correction factor F. As is evident from Tables 6 and 7 in Example 4, subjects 1 and 2 had significantly different subcutaneous adipose tissue thickness and distribution in subcutaneous adipose tissue. For example, subject 1 had an abdominal subcutaneous adipose tissue thickness of 5.3 mm (90 degree transmission angle), while subject 2 had an abdominal subcutaneous adipose tissue thickness of 33.1 mm, i.e. 6-fold greater. Conversely, both subject 1 and subject 2 had very similar subcutaneous adipose tissue thickness in the medial and lateral calf. Despite these significant differences in subcutaneous adipose tissue thickness and distribution, use of the same correction factor yielded results that were very similar to those obtained with hydrostatic weighing.

The correlation between percent body adipose tissue determined using ultra-sonic measurements of subcutaneous adipose tissue thickness and percent body adipose tissue estimated using hydrostatic weighing was excellent. The percent difference between ultra-sonic interrogation and the conventional hydrostatic weighing technique was on the order of 2%. Part of this variation may be related to inaccuracies in estimating limb, i.e. arm, thigh, and calf length, as well as inaccuracies in correction factors. However, part of the difference may also be explained by inaccuracies in hydrostatic weighing. Hydrostatic weighing requires estimation of pulmonary residual volume unless even more expensive pulmonary function tests are added to the examination to obtain a more accurate measure of residual volume. Additionally, hydrostatic weighing does not account for the great variability in bone density between individuals which will affect the accuracy of measurements of body density and resultant calculation of percent body adipose tissue adversely (American College of Sports Medicine, ACSM's guidelines for exercise testing and prescription, 53–63 (1995)). Submersion of the head under water may be difficult or anxiety provoking for some individuals. Finally, hydrostatic weighing requires expensive, special equipment and the process is time-consuming and complicated when compared to a hand-held ultra-sonic device.

PUBLICATIONS

Articles

1. American College of Sports Medicine, ACSM's guidelines for exercise testing and prescription, 53–63 (1995).
2. Booth, R. A. D., Goddard, B. A., Paton, A., Br J Nutr, 20: 719–725 (1966).
3. Brozek, J., Grande, F., Anderson, J., Keys, A., Ann NY Acad Sci, 110: 113–140 (1963).
4. Bushberg, J. T., Seibert, J. A., Leidholdt, E. M., Boone, J. M., The essential physics of medical imaging 1–742 (1994).
5. Chumlea, W. C., Roche, A. F., Am J Phys Anthropol, 71: 351–357 (1986).
6. Fanelli, M. T., Kuczmarksi, R. J., Hirsch, M., Int J Obesity, 12: 125–132 (1988).
7. Jackson, A. S., Pollock, M. L., Br J Nutr, 1978: 497–504 (1978).
8. Jebb, S. A., et al., Am J Clin Nutr, 58: 455–462 (1993).
9. Jones, P. R. M., Davies, P. S. W., Norgan, N. G., Am J Phys Anthropol, 71: 359–363 (1986).
10. Kuczmarski, R. J., Fanelli, M. T., Koch, G. G., Am J Clin Nutr, 45: 717–724 (1987).
11. Paijmans, I. J. M., Wilmore, K. M., Wilmore, J. H., J Am Coll Nutrit, 11: 145–151 (1992).
12. Ramirez, M. E., Am J Phys Anthropol, 89: 347–357 (1992).
13. Reali, U., Chiarugi, C., DeSiena, G. M., Giannotti, V., Plast Reconstr Surg, 93: 1050–1055 (1994).
14. Rolland-Cachera, M. F., Horm Res, 39 (suppl. 3): 25–40 (1993).

15. Sehgal, C. M., J Acoust Soc Am, 94: 1944–1952 (1993).
16. Siri, W. E., Univ Calif Donner Lab Med Phys Rep, March: (1956).
17. Volz, P. A., Ostrove, S. M., Med Sci Sports Exerc, 16: 97–102 (1984).

Patent Documents

U.S. Pat. No. 4,043,181. Issued Aug. 23, 1977.
U.S. Pat. No. 4,224,829. Issued Sep. 30, 1980.
U.S. Pat. No. 4,242,911. Issued Jan. 6, 1981.
U.S. Pat. No. 4,446,737. Issued May 8, 1984.
U.S. Pat. No. 4,540,946. Issued Sep. 10, 1985.
U.S. Pat. No. 4,658,827. Issued Apr. 21, 1987.
U.S. Pat. No. 4,688,428. Issued Aug. 25, 1987.
U.S. Pat. No. 4,702,258. Issued Oct. 27, 1987.
U.S. Pat. No. 4,830,015. Issued May 16, 1989.
U.S. Pat. No. 4,833,323. Issued May 23, 1989.
U.S. Pat. No. 4,920,966. Issued May 1, 1990.
U.S. Pat. No. 4,947,862. Issued Aug. 14, 1990.
U.S. Pat. No. Des. 320, 662. Issued Oct. 8, 1991.
U.S. Pat. No. 5,208,747. Issued May 4, 1993.
PCT WO 93/12419. Published Jun. 24, 1993.
U.S. Pat. No. 5,271,403. Issued Dec. 21, 1993.
U.S. Pat. No. 5,303,708. Issued Apr. 19, 1994.
U.S. Pat. No. 5,353,796. Issued Oct. 11, 1994.
U.S. Pat. No. 5,617,864 Issued Apr. 8, 1997.

All referenced documents and publications, including articles, patents and patent applications, are herein incorporated by reference as they would have been if they were incorporated by reference individually.

We claim:

1. A method of measuring adipose tissue in a human, comprising:
    transmitting at least a first ultra-sonic pulse and a second ultra-sonic pulse from at least a first position and a second position,
    measuring at least one first reflective distance from said first ultra-sonic pulse, wherein said first reflective distance is from the Skin to 1) an adipose tissue/muscle tissue or 2) an adipose tissue/fascia interface,
    measuring at least one second reflective distance from said second ultra-sonic pulse, wherein said second reflective distance is from the skin to 1) an adipose tissue/muscle or 2) an adipose tissue/fascia interface, and
    selecting from said first reflective distance and said second reflective distance a distance of shortest length to indicate an anatomical distance between the inner and outer border of subcutaneous adipose tissue.

2. The method of claim 1, wherein at least one of said ultra-sonic pulses is transmitted substantially perpendicular to said plane.

3. The method of claim 1, wherein said first ultra-sonic pulse has a first transmission angle with respect to said plane and said second ultra-sonic pulse has a second transmission angle with respect to said plane, wherein there is a predetermined divergent angle between said first ultra-sonic pulse and second ultra-sonic pulse or a convergent angle between said first ultra-sonic pulse and second ultra-sonic pulse,
    said measuring further comprises detecting said first ultra-sonic pulse and second ultra-sonic pulse with an ultra-sonic detector, and
    wherein said predetermined divergent angle or said predetermined convergent angle improves the measurement of an anatomical distance compared to the measurement of an anatomical distance in the absence of said predetermined divergent or convergent angle.

4. The method of claim 3, wherein said selecting corrects for an ultra-sonic transmission parallax of said first and second pulses relative to a plane in said subcutaneous adipose tissue.

5. The method of claim 3, further comprising a computational unit that corrects for non orthogonal probe alignment with said tissue, wherein said computational unit permits computational determination of a shortest reflective distance.

6. The method of claim 1, wherein said step of transmistting includes transmission from a first ultra-sonic generator and a second ultra-sonic generator and said first ultra-sonic generator and said second ultra-sonic generator have different transmission frequencies.

7. The method of claim 1, wherein said first ultra-sonic generator is for an A-scan.

8. The method of claim 1, wherein said measuring further comprises 1) a first series of trigger pulses that sequentially fires an array of ultra-sonic crystals starting from a first end to a second end of said array, 2) a series of trigger pulses that sequentially fires said array from a second end to a first end of said array.

9. The method of claim 8, wherein said object is a human and said first, second and third series of trigger pulses enhances measurement of a shortest reflective distance.

10. A handheld, compact ultra-sonic system, comprising:
    at least one first ultra-sonic source to transmit an ultra-sonic pulse to an object and adapted for placement on a surface,
    at least one first ultra-sonic detector receive an ultra-sonic signal from said object and adapted for placement on a surface,
    an electronic operating unit used for instructing transmission by said first ultra-sonic source and used for generating a reflective distance from a layer within said object using signals received from said first ultra-sonic detector; and
    a handheld housing that encases said first ultra-sonic source, said first ultra-sonic detector and said electronic operating unit that determines a distance of shortest length from said ultra-sonic signal that corresponds to a layer in said object.

11. The ultra-sonic system of claim 10, wherein said electronic operating unit further comprises a computational unit that permits parallax adjustment by determining a shortest reflective distance in said object.

12. The ultra-sonic system of claim 10, wherein said first ultra-sonic source transmits an ultra-sonic pulse with an acoustic mirror to generate at least one additional axis of transmission.

13. The ultra-sonic system of claim 10, wherein said first ultra-sonic source is adpated for A-scan.

14. The ultra-sonic system of claim 10, wherein said first ultra-sonic detector is electronically gated to reject at least one ultra-sonic echo during at least one predetermined time interval.

15. The ultra-sonic system of claim 14, wherein said at least one predetermined time interval is selected to improve measurement of body adipose tissue at a predetermined tissue depth compared to the absence of electronically gating said at least one first ultra-sonic detector.

16. The ultra-sonic system of claim 15, wherein said at least one predetermined time interval is selected automatically or manually to measure body adipose tissue at a predetermined tissue depth.

17. The ultra-sonic system of claim 16, wherein said predetermined time interval is 1) between about 0 to 5 microseconds or 2) greater than about 40 microseconds.

18. The ultra-sonic system of claim 10, wherein said first ultra-sonic detector is electronically gated with an electronic filter.

19. The ultra-sonic system of claim 10, further comprising a digital filter for filtering ultra-sonic signals.

20. The ultra-sonic system of claim 10, further comprising a kit for monitoring and enhancing adipose tissue loss comprising one or more of the following: nutritional supplements, a nutritional regime, exercise plan, weight loss agents, and a health club membership.

21. The ultra-sonic system of claim 10, wherein said first ultra-sonic source is included in a linear array that transmits ultra-sonic signals in response to a trigger pulse that sequentially fires each crystal in said linear array, wherein said sequential firing permits varying the depth of said ultra-sonic signals.

22. The ultra-sonic system of claim 21, wherein said linear array transmits ultra-sonic signals in response to 1) a first series of trigger pulses that sequentially fires each crystal or segments of crystals in said linear array starting from a first end to a second end of said array, and 2) a second series of trigger pulses that sequentially fires each crystal or segments of crystals in said linear array starting from said second end to said first end.

23. The ultra-sonic system of claim 22, wherein said first and second series of trigger pulses produce a series of pulses with divergent angles that improves measurement of a shortest reflective distance compared to the simultaneous firing of said array.

24. The ultra-sonic system of claim 10, wherein said first ultra-sonic source is included in a matrix of ultra-sonic crystals.

25. The ultra-sonic system of claim 24, wherein said matrix of ultra-sonic crystals is a rectangular matrix of the following formula:

A Bn C

A1n B1n C1n

A2n B2n C2n wherein A, A1, A2, B, B1, B2, C, C1, and C2 are individual ultra-sonic crystal electronic units capable of transmitting an ultra-sonic pulse, and n for each individual crystal symbol can be independently equal to 0 or any number between 1 and 20.

26. The ultra-sonic system of claim 25, wherein a first trigger pulse sequentially fires each ultra-sonic crystal electronic units in said array in the following order A Bn C; then A1nB1n C1n; then A2B2n C2n; then A, A1, A2; then B, B1, B2, and then C, C1, and C2.

27. The ultra-sonic system of claim 10, wherein said housing includes a display.

28. A method of monitoring adipose tissue in a human and the effect of a weight loss agent, comprising:

administering to a human a weight loss agent, transmitting at least a first ultra-sonic pulse from at least a first position, measuring at least one first reflective distance from said first ultra-sonic pulse, wherein said at least one first reflective distance is from the skin to 1) an adipose tissue/muscle tissue or 2) an adipose tissue/fascia interface, measuring at least one second reflective distance from said second ultra-sonic pulse, wherein said second reflective distance is from the skin to 1) an adipose tissue/muscle or 2) an adipose tissue/fascia interface, and determining from said first reflective distance and said second reflective distance an anatomical distance between the inner and outer border of subcutaneous adipose tissue, wherein a decrease in said anatomical distance can indicate said weight loss agent reduced said subcutaneous adipose tissue, an increase in said anatomical distance can indicate said weight loss agent increased said subcutaneous adipose tissue and no change in said anatomical distance can indicate said weight loss agent did not effect said subcutaneous adipose tissue.

29. The method of monitoring adipose tissue of claim 28, wherein in said step of administering said weight loss agent is a prescription drug.

30. The method of monitoring adipose tissue of claim 28, wherein said prescription drug was not previously known to decrease adipose tissue layer thickness in a human.

31. The method of monitoring adipose tissue of claim 29, further comprising measuring at least one second reflective distance from a second ultra-sonic pulse at a transmission angle different from said first ultra-sonic pulse, wherein said second reflective distance is from the skin to an adipose tissue/muscle.

32. The method of monitoring adipose tissue of claim 31, further comprising selecting from said first reflective distance and said second reflective distance a distance of shortest length to indicate an anatomical distance between the inner and outer border of subcutaneous adipose tissue.

33. The method of monitoring adipose tissue of claim 29, further comprising historical tracking of ultra-sonic measurements of adipose tissue in said human.

34. The method of monitoring adipose tissue of claim 29, further comprising determining adipose tissue layer thickness at least two different anatomical sites on said human.

* * * * *